United States Patent [19]

Denen et al.

[11] Patent Number: 4,801,803

[45] Date of Patent: Jan. 31, 1989

[54] DETECTOR AND LOCALIZER FOR LOW ENERGY RADIATION EMISSIONS

[75] Inventors: Dennis J. Denen; Marlin O. Thurston; Raymond C. Ramsey, all of Columbus, Ohio

[73] Assignee: Neoprobe Corporation, Columbus, Ohio

[21] Appl. No.: 27,197

[22] Filed: Mar. 17, 1987

[51] Int. Cl.$^4$ ............................................. G01T 1/161
[52] U.S. Cl. .............................. 250/336.1; 250/370.01
[58] Field of Search .......... 250/370 JX, 370 J, 370 R, 250/370 F, 336.1; 357/29; 128/654

[56] References Cited

FOREIGN PATENT DOCUMENTS 2117900 10/1983 United Kingdom ............. 250/336.1

OTHER PUBLICATIONS

Richard D. Baxter, "Miniature Hybrid Preamplifier for CdTe Detectors." *IEEE Transactions on Nuclear Science*, vol. NS-23, No. 1 (Feb. 1976) pp. 493-497.

P. J. O'Dwyer et al., "Intraoperative Probe-Directed Immunodetection Using a Monoclonal Antibody" *Archives of Surgery*, vol. 121 (Dec. 1986) pp. 1391-1394.

D. T. Martin et al., "Intraoperative Radioimmunodetection of Colorectal Tumor with a Hand-Held Radiation Detector" *American Journal of Surgery*, vol. 150, No. 6, (Dec. 1985) pp. 672-675.

D. R. Aitken et al., "Portable Gamma Probe for Radioimmune Localization of Experimental Colon Tumor Xenografts" *Journal of Biological Research*, vol. 36, No. 5 (1984) pp. 480-489.

E. W. Martin, Jr., et al., "Radioimmunoguided Surgery: Intraoperative Use of Monoclonal Antibody 17-1A in Colorectal Cancer" *Hybridoma*, vol. 5, Supplement 1 (1986) pp. S97-S108.

*Primary Examiner*—Janice A. Howell
*Assistant Examiner*—Constantine Hannaher
*Attorney, Agent, or Firm*—Mueller and Smith

[57] ABSTRACT

A detector particularly suited for use in immuno-guided surgery capable of detecting very faint gamma emissions and thereby localizing cancerous tumor. The detector employs a hand manipular probe within which is contained a crystal such as cadmium telluride which is secured in a light tight compressively restrained environment employing compliant yet conductive components which also serve to exhibit varying accoustical impedance to impinging microphonic effects. A preamplifier is incorporated within the probe device itself which employs an integrator stage front end combining a field effect transistor and bipolar device with a very small feedback capacitance of less than one picofarad. A bootstrap technique is utilized to enhance the amplification of the bipolar amplification stage. Pulse related signals outputted from the device are normalized and compared to produce pulse data which are analyzed. In one mode of operation a siren effect is employed to guide the surgeon towards emission sources.

39 Claims, 17 Drawing Sheets

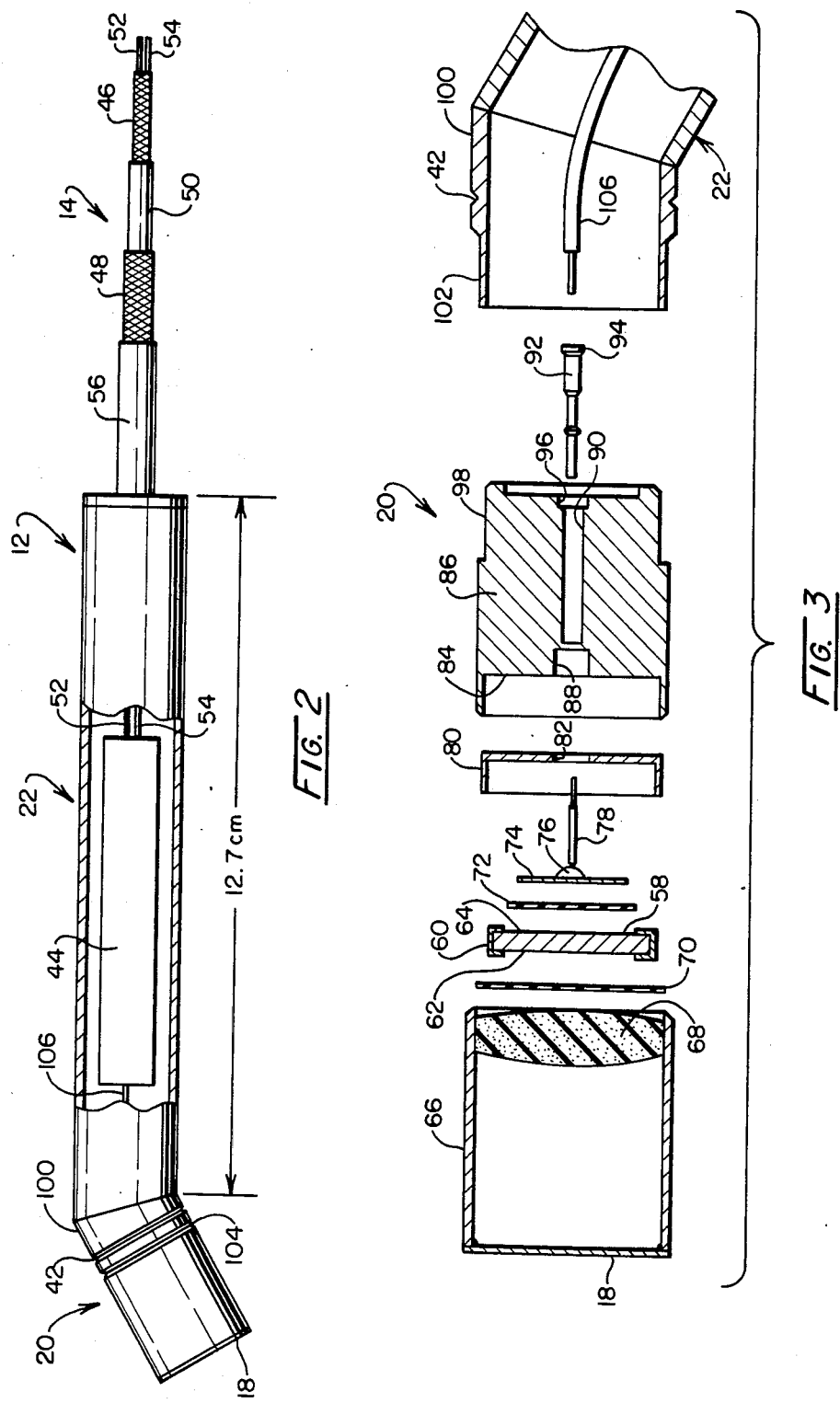

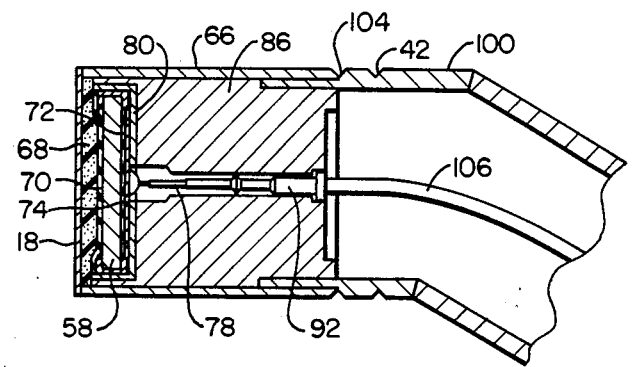
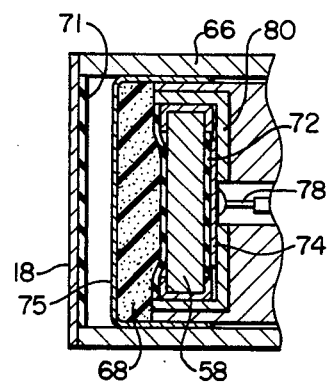
FIG. 4  FIG. 4A
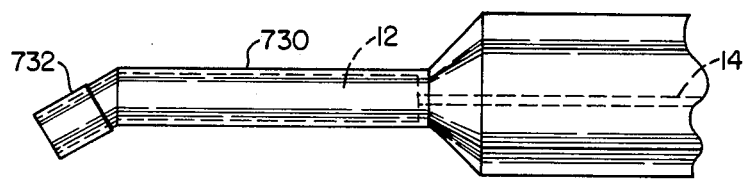
FIG. 11
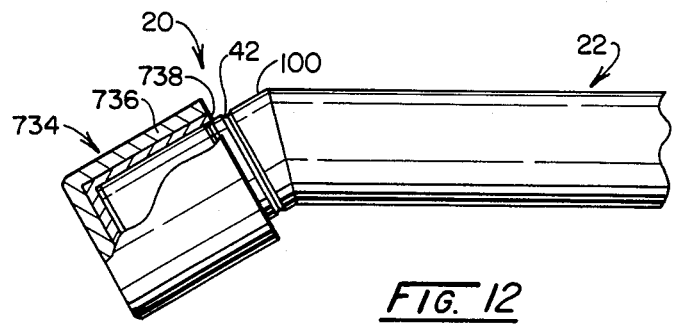
FIG. 12
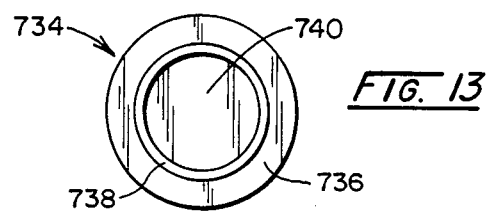
FIG. 13

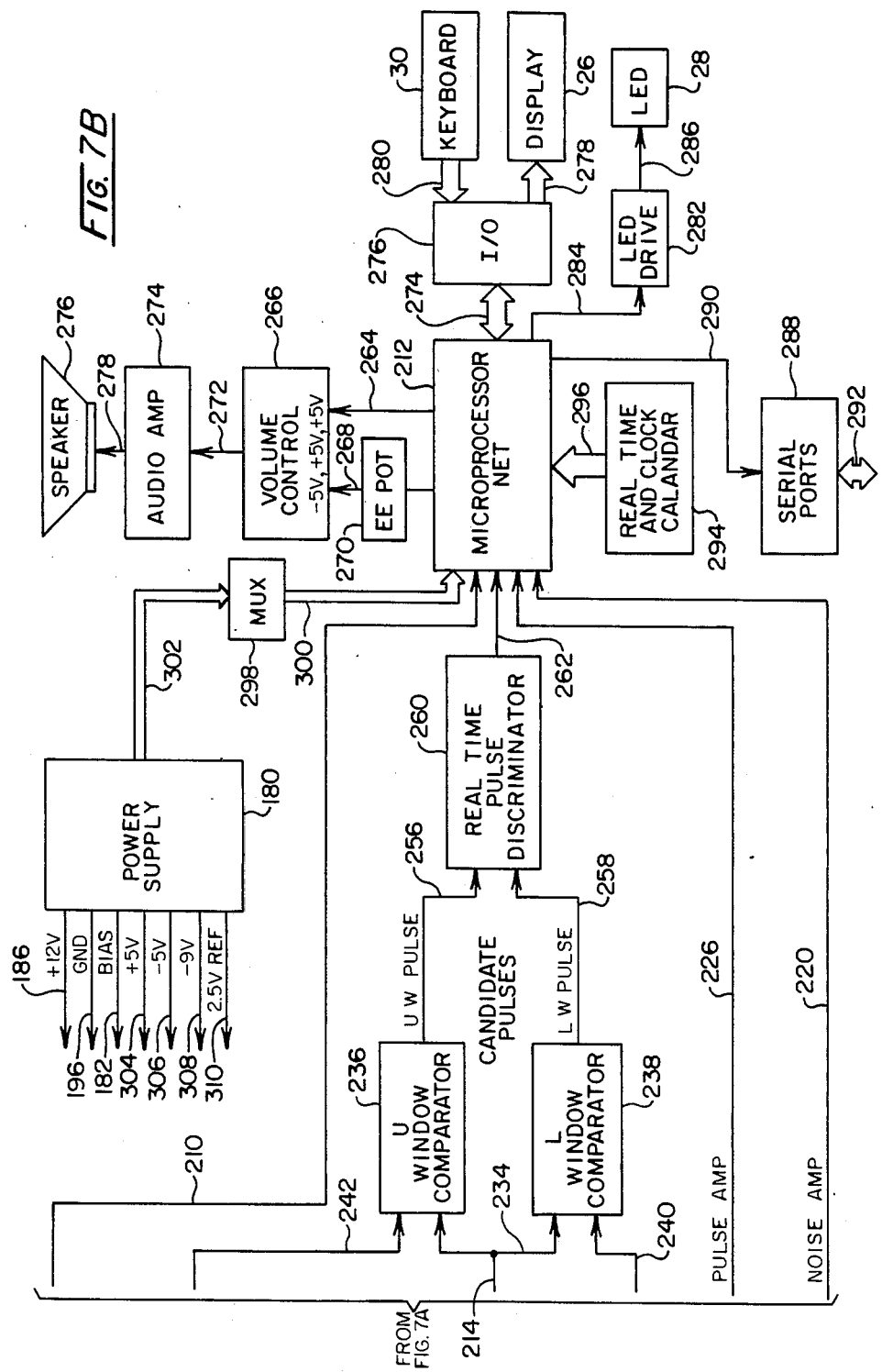

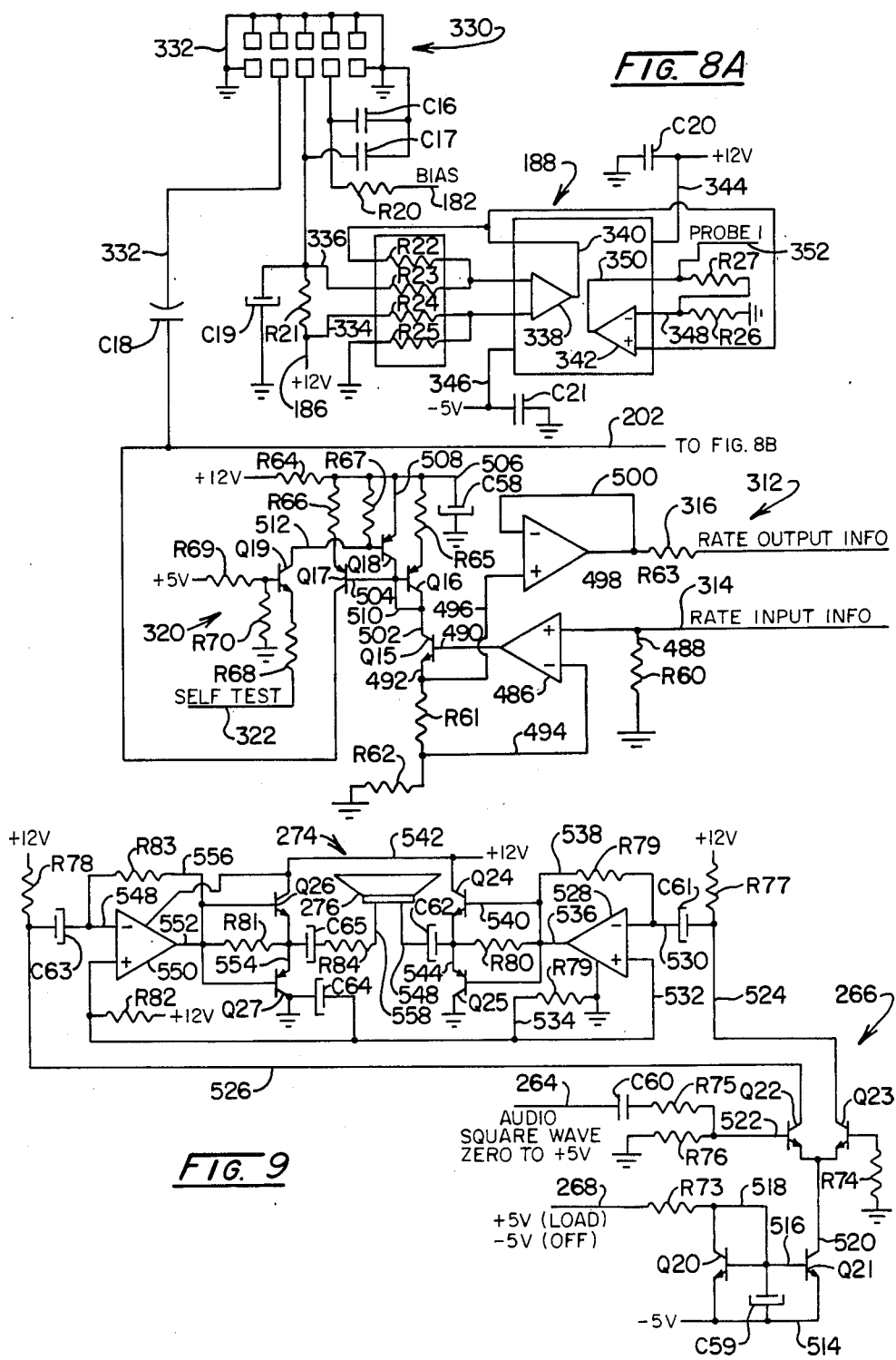

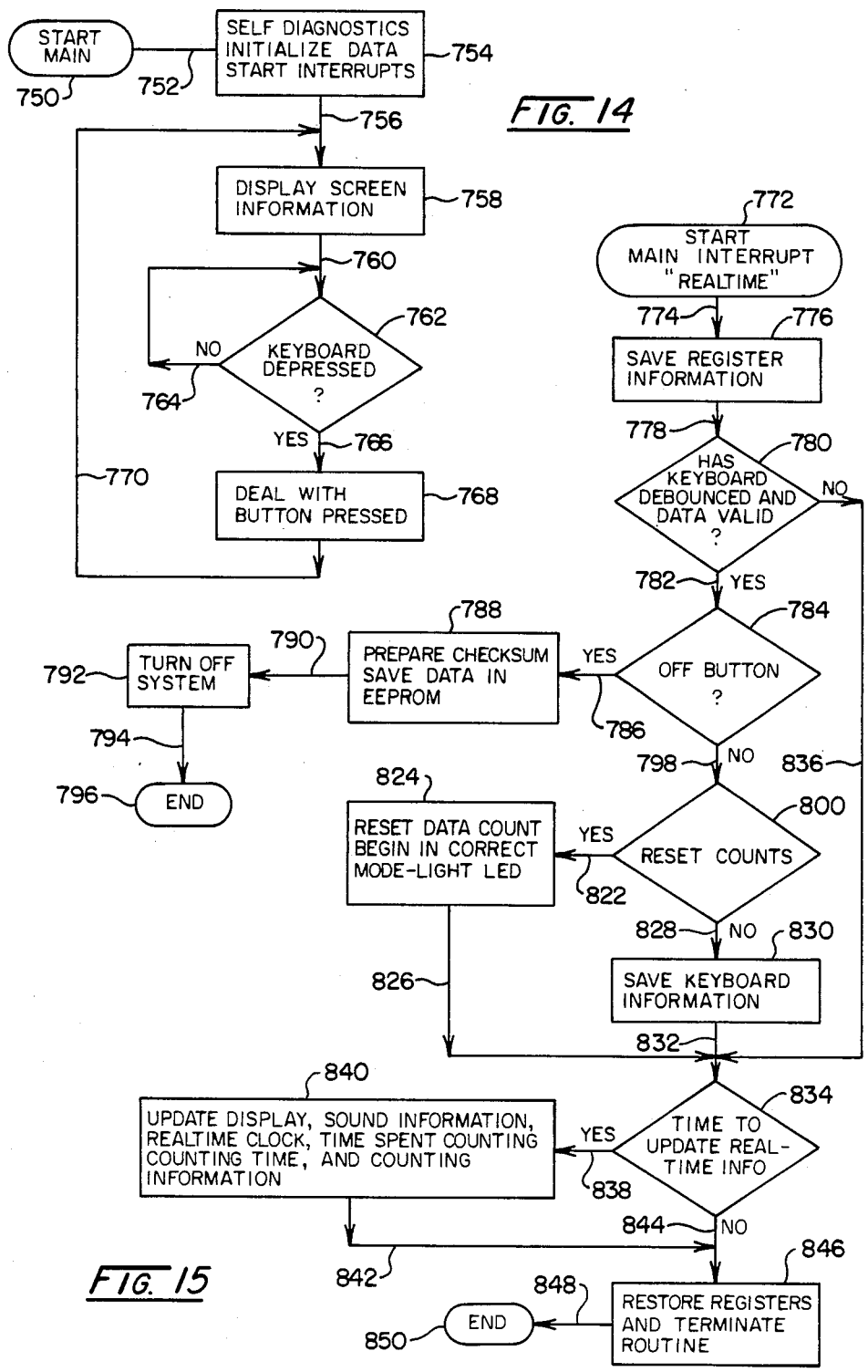

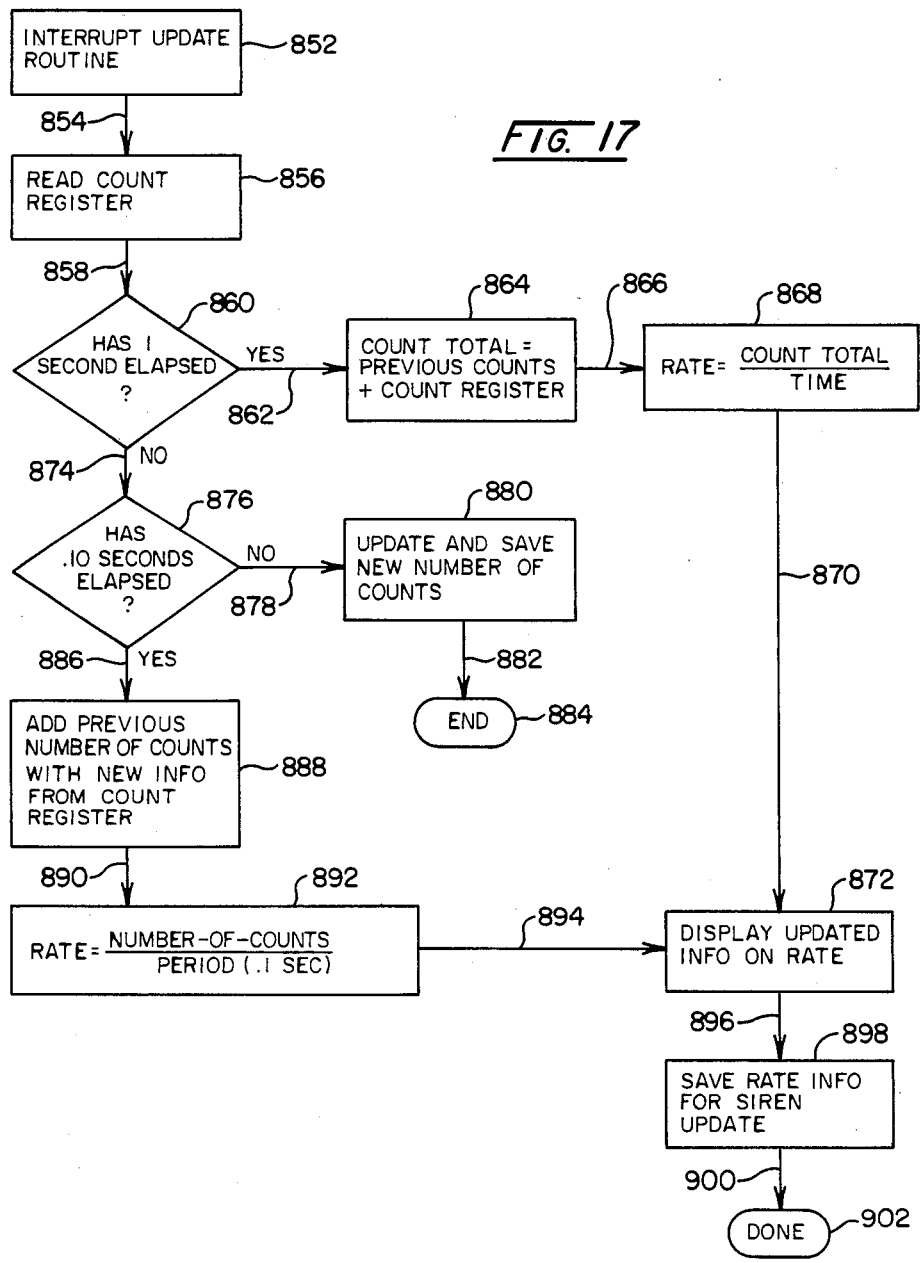

DETECTOR AND LOCALIZER FOR LOW ENERGY RADIATION EMISSIONS

BACKGROUND

The detection and treatment of cancerous tissue has been the subject of intense investigation for many years. One among the many approaches to its detection has concerned the identification of tumor specific antigens. Where these antigens can be identified, radionucleid labeled antibodies have been employed which tend to collect at tumor sites. When so concentrated, somewhat elaborate radiation detection equipment then is employed to record, for example, by imaging the concentrations of the emissive substances and thus to locate neoplastic tissue. Important advances in this procedure have been evidenced through the use of monoclonal antibodies or fragments thereof with a variety of radionucleides. Typical techniques for carrying out imaging of the antibodies have involved, for example, tomographic scanning, immunoscintigraphy and the like. The particular choice of radionucleid for labeling antibodies is dependent upon its nuclear properties, the physical half life, the detection instrument capabilities, the pharmacokinetics of the radiolabeled antibody, and the degree of difficulty of the labeling procedure. The most widely used of these radionucleides in nuclear medicine imaging include technetium, $Tc^{99m}$, iodine $I^{123}$, $I^{131}$, and indium $In^{111}$. Of the above, for localizing tumors of the gastro-intestinal tract, the radionucleid $I^{131}$ is used as the marker or label in conjunction with imaging gamma cameras and the like which are relatively large and elaborate devices positioned above the patient during the imaging process.

In spite of its somewhat extensive utilization, $I^{131}$ is not an ideal radionucleid for use in diagnostic medicine. The high energy gamma-photon emitted from $I^{131}$ is poorly detected by classic gamma camera and like instrumentation. In addition, the particular admissions of emissions deliver a high radiation dose to the patient. Further, the imaging definition of these external imaging devices have not been satisfactory for many reasons. As tumor sites become smaller, the radionucleid concentrations thereat will tend to be lost, from an imaging standpoint, in the background or blood pool radiation necessarily present in the patient.

Over the recent past, a surgical procedure has been developed concerning the differentiation and removal of such neoplastic tissue through the use of much lower energy gamma emission labels for example, $I^{125}$ (27-35 kev). While such a radiolabel cannot be employed with conventional external imaging or scanning devices, it has been found that when employed with a probe type detection structure, a highly effective differentiation technique can be evolved. More particularly, the longer half life of this type of radiolabel coupled with a surgical methodology involving the waiting of appropriate intervals from the time of introduction of the radiolabelled inantibody to the patient to the time of surgery, can evolve a highly accurate differentiation of cancerous tumor. This improved method of localization, differentiation and removal of cancerous tumor involves a surgical procedure wherein the patient suspected of containing neoplastic tissue is administered an effective amount of a labeled antibody specific for neoplastic tissue and labeled with a radioactive isotope as above-noted exhibiting photon emissions of specific energy levels. Next, the surgical procedure is delayed for a time interval following such administration for permitting the labeled antibody to preferentially concentrate in any neoplastic tissue present in the patient so as to increase the ratio of photon emissions from the neoplastic tissue to the background photon emissions. Thereafter, an operative field of the patient is surgically accessed and tissue within the operative field to be examined for neoplastic tissue has the background photon emission count determined. Once the background photon emission count for the tissue within the operative field has been determined, this hand-held probe is manually positioned within the operative field adjacent tissue suspected of being neoplastic. Readouts then can be achieved from probe counting for differentiation. In the above regard, reference is made to the following technical publications:

I. "CEA-Directed Second-Look Surgery in the Asymptomatic Patient after Primary Resection of Colorectal Carcinoma", E. W. Martin, Jr., MD, J. P. Minton, MD, PhD, Larry C. Carey, MD. *Annals of Surgery* 202: 1 (September 1985 301-12.

II. "Intraoperative Probe-Directed Immunodetection Using a Monoclonal Antibody", P. J. O'Dwyer, MD, C. M. Mojzsik, RN MS, G. H. Hinkle, RPh, MS, M. Rousseau, J. Olsen, MD, S. E. Tuttle, MD, R. F. Barth, PhD, MO. Thurston, PhD, D. P. McCabe, MD, W. B. Farrar, MD, E. W. Martin, Jr., MD. *Archives of Surgery*, 121 (December 1986) 1321-1394.

III. "Intraoperative Radioimmunodetection of Colorectal Tumors with a Hand-Held Radiation Detector", D. T. Martin, MD, G. H. Hinkle, MS RPh, S. Tuttle, MD, J. Olsen, MD, H. Abdel-Nabi, MD, D. Houchens, PhD, M. Thurston, PhD, E. W. Martin, Jr., MD. *American Journal of Surgery*, 150: 6 (December 1985) 672-75.

IV. "Portable Gamma Probe for Radioimmune Localization of Experimental Colon Tumor Xenografts", D. R. Aitken MD, M. O. Thurston, PhD, G. H. Hinkle, MS RPh, D. T. Martin, MD, D. E. Haagensen, Jr., MD, PhD, D. Houchens, PhD, S. E. Tuttle, MD, E. W. Martin, Jr., MD. *Journal of Surgical Research*, 36: 5 (1984) 480-489.

V. "Radioimmunoguided Surgery: Intraoperative Use of Monoclonal Antibody 17-1A in Colorectal Cancer". E. W. Martin, Jr., MD, S. E. Tuttle, MD, M. Rousseau, C. M. Mojzsik, RN MS, P. J. O'Dwyer, MD, G. H. Hinkle, MS RPh, E. A. Miller, R. A. Goodwin, O. A. Oredipe, MA, R. F. Barth, MD, J. O. Olsen, MD, D. Houchens, PhD, S. D. Jewell, MS, D. M. Bucci, BS, D. Adams, Z. Steplewski, M. O. Thurston, PhD, *Hybridoma* 5 Suppl 1 (1986) S97-108.

Reference further is made to commonly assigned application for U.S. patent Ser. No. 06/905,880 entitled "Method for Locating, Differentiating, and Removing Neoplasms" by Edward W. Martin, Jr., and Marlin O. Thurston, filed Sept. 10, 1986.

The success of this highly effective differentiation and localization technique is predicated upon the availability of a probe-type detecting device capable of detecting extemely low amounts of radiation necessarily developed with the procedure. In this regard, low energy radionucleides are used such as $I^{125}$ and the distribution of radiolabeled antibody with the nucleid is quite sparse so that background emissions can be minimized and the ratio of tumor-specific counts received to background counts can be maximized. Conventional radiation detection probe-type devices are ineffective for this purpose. Generally, because a detection device is required for the probes which is capable of performing at room temperatures, a detection crystal such as cadmium telluride is employed. The probe using such a crystal must be capable of detecting as little as a single gamma ray emission which may, for example, create electron-hole pairs in the crystal of between about 2,000 and 4,000 electrons. Considering that an ampere generates $6.25 \times 10^{18}$ electrons per second, one may observe that extremely small currents must be detectable with such probe. However, the probe system also must be capable of discriminating such currents from any of a wide variety of electrical disturbances, for example which may be occasioned from cosmic inputs, room temperature molecular generated noise and capacitively induced noise developed from the mere manipulation of the probe itself. While being capable of performing under these extreme criteria, the same probe further must be capble of performing under the requirements of the surgical theater. In this regard, it must be sterilizable and rugged enough to withstand manipulation by the surgeon within the body cavity of the patient. Further, the system with which the probe is employed, must be capable of perceptively apprising the surgeon of when neoplastic tissue is being approached such that the device may be employed for the purpose of guiding the surgeon to the situs of cancer. Finally, for surgical use, the probe instrument must be small, so as to be effectively manipulated through surgical openings and the like. Such dimunitive size is not esily achieved under the above operational criteria. This technique has been described as "radioimmuno-guided surgery", a surgical approach developed by E. W. Martin, Jr., MD, and M. O. Thurston, PhD.

SUMMARY

The present invention is addressed to apparatus and system for detecting and locating sources of emitted radiation and, particularly, sources of gamma radiation. Detection is achieved under room temperature conditions using a crystal such as cadmium telluride and with respect to very low energy emissions. To achieve the extreme sensitivity capabilities of the appartus, an instrumentation approach has been developed in which the somewhat fragile crystal is securely retained in isolation from externally induced incidents otherwise creating excessive noise. In this regard, microphonic effects are minimized through employment of a sequence of materials exhibiting divergent accoustic impedances. Capacitive effects occasioned by the most minute of intercomponent movements are controlled to acceptable levels.

The probe instrument design incorporates a preamplifier with in integrator structure which resides in substantial adjacency with the crystal within the probe instrument and which achieves very substantial amplifying gain of relatively minute crystal derived charge signals. This sensitivity permits medical uses of the instrument, for example, in immuno-guided surgery where low energy gamma emissions are located to differentiate cancerous tumor. The system of the invention employs an audibly perceptible output in conjunction with a count rate analysis of detected emissions to guide the surgeon to tumor sites with a siren effect wherein the frequency of the audible output increase as the count rate increases and vice versa.

Another feature of the invention is to provide an instrument for detecting and locating sources of radiation emissions which includes a housing having a first portion having sidewalls formed of select gamma radiation attenuating material and exhibiting an electrical shielding effect and extending to a forward opening positionable proximate the source. The housing further includes a hand-graspable second portion extending from the first portion. A window permitting gamma radiation transmission is positioned at the forward opening of the housing first portion which further functions to block passage of light. A gamma radiation responsive crystal is positioned within the first portion of the housing having a forward surface disposed toward the window and a rearward surface. A thin gamma radiation transmissive and electrically conductive first insert is positioned adjacent the crystal forward surface, while an electrically conductive contact is positioned against the crystal rearward surface to effect application of an electrical bias and further to conduct gamma ray induced signal charges therefrom. A block formed of gamma radiation attenuating material is positioned within the first portion of the housing and adjacent the rearwardly disposed portion of the contact for blocking entry of radiation toward the crystal rearward surface. A compression arrangement is placed within the housing first portion for effecting a conforming compressive relationship between the crystal forward surface and the first insert as well as between the crystal rearward surface and the contact. The compression arrangement is spaced from the window a predetermined amount establishing a dead space therebetween and includes a compressible foamaceous material and a retainer transparent to radiation for retaining the foamaceous material in compression against the crystal forward surface. A circuit is positioned within the housing for applying electrical bias through the contact to the crystal and which includes an amplifier for receiving and electrically treating the signal charges to provide output signals.

Another feature of the invention provides a radiation detection instrument which includes a detector for deriving induced charges in response to gamma ray interaction therewith when selectively biased from a source. An integrator network is provided having an input for receiving the induced charges which includes a field effect transistor having a gate coupled with the input and drain and source terminals and functioning to effect amplification of the induced charges as an output at one of the noted terminals. A bipolar transistor arrangement is provided having a base electrode coupled with the field effect transistor, having an emitter terminal coupled with a first impedance selected deriving an operating bias, and a collector terminal responsive to a collector impedance including collector resistance means effecting an amplification of the signal output to derive a first voltage amplification signal. A bootstrap transistor stage is responsive to couple energy corresponding with the signal output to the collector resistor for raising the effective collector impedance in correspondence therewith. Further, a capacitor is coupled intermediate the integrator output and input for providing a capacitance of value selected below about one picofarad. In particular, it has been found that a value of capacitance of about 0.25 picofarads is preferred.

Another feature of the invention is to provide apparatus for detecting sources of gamms radiation which includes a housing having a forward portion extending to a forward opening positionable proximate the source and a rear portion extending from the forward portion. A window is positioned over the forward opening to permit transmission of radiation through the forward opening. Further, a crystal responsive to the noted radiation is positioned within the forward portion having a forward surface disposed toward the window and a rearward surface. An electrically conductive contact is positioned against the crystal rearward surface for effecting application of electrical bias thereto and for conducting gamma ray induced charge signals therefrom. A circuit is located within the housing rear portion which includes a source of select bias voltage as well as a connection arrangement coupled with the contact for applying the bias thereto and conveying current signals. An integrator network also is included having an input coupled with the connection and which includes a field effect transistor having a gate coupled with the input and drain and source terminals for effecting amplification of the induced charges as a signal output at a terminal. A bipolar transistor is provided having a base electrode coupled with the field effect transistor, having an emitter terminal coupled with a first impedance selected deriving an operating bias, and a collector terminal responsive to a collector impedance including a collector resistor for effecting amplification of the signal output to derive a first voltage amplification signals. A bootstrap transistor stage is responsive to couple energy corresponding with the signal output to the collector resistor for raising the effective collector impedance in correspondence therewith and a transmission circuit is provided for treating and transmitting the amplified voltage signals.

Another feature of the invention is to provide an apparatus for detecting and evaluating sources of gamma radiation having given energy levels. The apparatus includes a detector for deriving induced charges in response to interactions of radiation therewith to provide detector signals at given levels and exhibiting noise characteristics of given level. A noise averaging network is provided which is responsive to the given noise characteristics for deriving a noise signal corresponding with an average level of the given noise characteristics. A normalizing circuit is provided which is responsive to the detector signals and given noise characteristics and to a control input for adjusting the level of the noise characteristics and corresponding detector signal given levels to provide composite signals of normalized values. A comparator arrangement responds to the composite signal for comparing the amplitude thereof with presettable upper and lower threshold levels for providing pulse data outputs corresponding with the comparisons. A logic circuit responds to the pulse data outputs for deriving valid pulse signals and an output is incorporated which is controllable for providing a valid pulse signal related perceptible output. Finally, a control is included which is responsive to the noise averaging noise signal for deriving the control input to the normalizing circuit and to valid pulse signals for controlling the output arrangement.

Another feature of the invention is to provide a system for detecting and locating sources of gamma radiation which includes a hand manipular probe having a housing with a forward portion extending to a window positionable in the vicinity of the source and a handgraspable portion extending from the forward portion. A detector circuit is positioned within the housing for deriving induced charges in response to gamma ray interaction therewith and providing output signals corresponding therewith. A transmission arrangement serves to transmit the output signal and a signal treatment configuration is provided which includes an energy level analysis network for evaluating the output signals with respect to noise phenomena and deriving pulse data output signals. An annunciator is provided which is responsive to drive signals for providing an audibly perceptible output variable in response to the frequency of the drive signals and a control responsive to the pulse data output signals for deriving the rates of occurrences thereof for predetermined intervals and is responsive to each of select ranges of the derived rates for generating a predetermined corresponding drive signal of unique frequency.

Other objects of the invention will, in part, be obvious and will, in part, appear hereinafter.

The invention accordingly, comprises the apparatus and system possessing the construction, combination of elements and arrangement of parts which are exemplified in the following detailed disclosure. For a fuller understanding of the nature and objects of the invention, reference should be had to the following detailed description taken in connection with the accompanying drawings.

BRIEF DESCRIPTION OF THE DRAWINGS

FIG. 2 is a side elevational view of the probe instrument shown in FIG. 1 with portions broken away to reveal internal structures;

FIG. 3 is an exploded view of the forward assemblage of the instrument of FIG. 2;

FIG. 4 is a sectional view of the forward portion of the instrument of FIG. 2;

FIG. 4A is a sectional view of an alternate embodiment of the forward portion of the instrument as described in conjunction with FIG. 4;

FIGS. 7A and 7B combine as labelled to form a block diagram of the functional components of the system of the invention;

FIGS. 8A–8C combine as labeled to provide an electrical schematic diagram of the analog signal treatment components of the apparatus of the invention;

FIG. 9 is an electrical schematic diagram of the volume control and audio amplification components of the apparatus of the invention;

FIG. 11 is a side view of the probe instrument of FIG. 2 showing its employment with a sterile cover;

FIG. 12 is a partial side view of the probe instrument of Fig. showing its association with a check source insert;

FIG. 13 is a top view of the check source insert represented in FIG. 12;

FIG. 14 is a flow chart showing the main program of the apparatus of the invention;

FIG. 15 is a flow chart showing an interrupt routine employed with the control features of the invention;

FIG. 17 is a flow chart showing a count rate determination carried out with the interrupt update routine of the control of the invention;

DETAILED DESCRIPTION OF THE INVENTION

Figure 1:
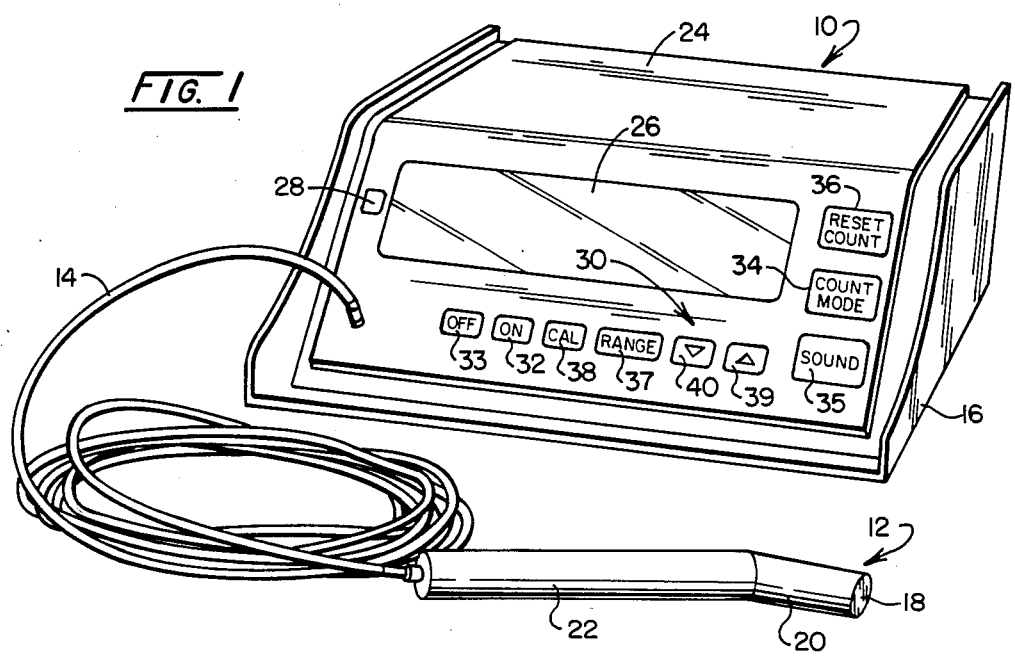
FIG. 1 is a perspective view of the probe instrument and associated console representing the instrumentation system of the invention.

Referring to FIG. 1, an embodiment of the instrument of the invention particularly designed for employment in the medical-surgical field is represented generally at 10. This instrument includes a hand-manipular probe instrument represented generally at 12 which is coupled by a triaxial cable 14 to a console 16. The probe 12, which preferably is retained by the surgeon within a disposable polymeric sheath or cover is maneuvered about the region of surgical interst to locate tumerous tissue for resection. When used in conjunction with colonic surgery, for example, the probe 12 is maneuvered through a surgical opening in the body cavity and essentially brought into contact with organs under study by the surgeon. When employed in a radioimmuno-guided mode, a loudspeaker or annunciator within the console 16 may be employed to provide a "siren" form of output which apprises the surgeon that the probe 12 is nearing a site of cancer. Thus, it is necessary that the device 12 be of convenient length and comfortable to grasp. The probe 12 is seen to include a window 18 located at the tip of an angularly oriented portion thereof 20. Portion 20 extends from a handgrippable portion 22 at an angle of about 30° to facilitate its manueverability about the back or hidden side of organs.

Because the assemblage 10 is used in a surgical theater, the console 16 also is readily cleaned, having a smooth, one-piece touch sensitive polymeric surface 24 surmounting a relatively large LCD readout or display 26, a dual colored LED readout 28 and a sequence of finger-actuated switches having a tactile feedback. These switches or keyboard as represented generally at 30 permit the microprocessor driven console 16 to carry out an instructive or "user friendly" dialogue with the practitioner. For purposes of safety, the device is powered by a rechargeable battery.

In addition to conventional on and off switches shown, respectively, at 32 and 33, the switches provided on the console 16 include a count mode switch 34, a sound switch 35, a reset count switch 36, a range function switch 37, a calibration function switch 38, and up and down incrementing switches for adjustment within certain of the switch generated modes as shown, respectively, at 39 and 40.

The probe 12 must be capable of performing essentially at room temperature. Thus, the device employs a cadmium telluride crystal and, because of the preferred low energy levels of radiation which it may detect, must be capable of operatively reacting a low energy gamma ray interactions. The interaction of gamma rays with such crystals is primarily through three processes, namely the photo-dielectric effect, Compton scattering, and pair production. In the photo-electric effect, a photon of energy, hv, interacts with an atom as a whole. Its energy is completely transferred to an electron, usually in the innermost shell. The electon is ejected with a kinetic energy: $e_{kin} = hv - E_b$, where $E_b$ is the binding energy of the orbital electron, h is Planck's constant, and v is the frequency associated with the wave nature of the gamma radiation. In Compton scattering, the primary photon may interact with any one of the orbital electrons. The electrons are considered essentially as free electrons under the condition that the primary photon energy is large compared with the electron binding energy. The interaction may be analyzed as the elastic collision between the primary photon and the electron. Energy is shared between the recoil electron and the secondary photon. This secondary photon travels in a direction different from that of the primary photon, and is referred to as the scattered photon.

Thus, as an incoming gamma ray is absorbed by the crystal, it transfers some or all of its energy to electrons, which as charged particles pass through the semi-conductor producing electron-hole pairs and, therefore, the capability of charge-transfer within the crystal median.

When a charge particle produces electron-hole pairs in the semi-conductor, the electric field causes these charge carriers to move toward and accumulate at the appropriate electrodes. As these charges are collected at the electrodes, they induce a charge or electrical pulse signnal in the circuit external to the detector. It is then necessary to pre-amplify these signals and feed them to the electronics of the control unit or console 16.

For effective performance, the probe 12 must be capable of generating and discerning signals representing gamma ray strikes which are of extremely low energy. In this regard, a gamma ray interaction with the cadmium telluride crystal may produce two or four thousand electrons. It being recognized that $6.25 \times 10^{18}$ electrons per second represent one ampere of current, the relative sensitivity of the instant device will become apparent. As a consequence, the mechanical structuring of the mounting arrangement for the crystal within the probe 12 is of critical importance as is the technique for detecting and treating these significantly small charges representing gamma ray interactions.

Looking to FIG. 2, a more detailed representation of the probe device 12 is revealed. The angular orientation of the front portion 20 is shown having the noted 30° cant with respect to the central axis of the hand gripped portion 22. Device 12 is small having an overall length of about 19 cm and portion 22 having a length of about 12.7 cm. The overall diameter of the crylinder structure 12 is about 1.9 cm. Front portion 20 is formed having a groove 42 for retaining collimator which optionally may be positioned over the portion 20 and window 18 to provide a higher directional aspect of the device. The hand grip portion 22 carries a preamplifier on an elongate circuit board as represented in general at 44. Depending upon the energies of radiation encountered, the probe 12 structure is formed of an electrically conductive and thus shielding material which further functions to attenuate radiation.

Cable 14 supplies power to the preabmplifier of the probe, as well as bias to the crystal and functions to transmit the preamplifier treated output signals. Cable 14 includes tin copper cladding components 46 and 48 which are mutually insulated and spaced by a silicon rubber tube 50 which is somewhat loose to permit flexure. The innermost leads of the arrangement at respective lines 52 and 54 carry the output signals from the preamplifier 44 and a bias signal, for example 30 volts, for application to the rear side of the crystal within the device 12. Clad 46 carries a 12 v power supply for the preamplifier circuit, while outer clad 48 carries ground for the system. An outer silicon rubber cover then is provided at 56.

Looking to FIG. 3, an exploded detail of the nose or forward portion 20 of probe 12 is provided. This portion 20 retains the cadminum telluride crystal in a light-tight and mechanically secure orientation while maintaining necessary ground and bias conditions upon it. Generally, such crystals as at 58 will have a rigidity or physical consistency somewhat similar to chalk and are formed having very light gold coatings on their surfaces. Device 58 is retained within an outer electrically insulative coating 60 of U-shaped cross section. The forward or front surface 62 is grounded oand, in effect, represents the most negative electrode in the system. It rearward face 64, on the other hand, has a bias, for example 30 v, applied to it, an available bias range of 10 v to 100 v generally being desired. Thus, these electrical parameters are required with respect to the crystal 58 while it is maintained in a carefully electrically shielded, acoustically dead and light-tight environment. The outer surface of front portion 20 is formed as an electrically conductive tube or collar 66 formed, for example, of copper so as to provide an electrical shield as well as an attenuator for radiation of the energy range contemplated. The forward edge of tube 66 is closed by the window 18 which are formed of a silocon-aluminum alloy about 0.38 mm thick soldered thereto.

Crystal 58 and various components associated with its mounting are assembled within the cup-shaped structure including window 18 and shell 66 in a sequence represented in FIG. 3 which includes a foamaceous, electrically conductive insert 68 having a diametric extent such that it is in contact with ground, here the internal electrically conductive surface of shell 66. Generally, the insert 68 may be provided as a carbon impregnated foam with functions to assist in the compression of the components under final assembly. Insert 68 is shown in FIG. 3 exhibiting its expanded, preassembly cross-sectional configuration.

Next in the assembly sequence is a disk-shaped insert 70 formed of carbon filled silicon rubber having a thickness, for example, of 0.5 mm. The diametric extent of the insert 70 is such that is it in contact with electrical ground about the internal periphery of the tube portion 66. Marketed, for example, by Tecknit Company of Cranford, N.J., insert 70 is both pliant and exhibits an adhesive-like surface which, in final assembly, tends to adhere to the forward surface 62 of the crystal 58. It has been found that the use of this disk, substantially improves the noise immunity of the device. Thin aluminum foil has been employed in place of the carbon filled rubber for insert 70, however, any slight rubbing of the foil insert against the face 62 will create a static electricity build-up and, thus, noise. While considerable improvement was found in employing the aluminum disk, it also was found that the probe functioned only when held montionless during a count, the mere sliding of a fingertip across the surface of the probe causing unacceptable noise levels with the latter arrangement. A similar disk of the conductive silicon rubber material but of lesser diametric extent is positioned for engagement with the rearward surface 64 of the crystal 58 as represented at 72. The noted crystal bias voltage is asserted through this adhesive surface insert 72 from a disk-shaped copper electrode 74. Provided having a thickness, for example, of about 1.277 mm, the electrode 74 may be gold-plated at least on its contact surface to improve conduction and avoid corrosive effects. The rearward side of the insert 74 carries a bead of solder 76 to effect a union with a short length of insulated wire 73. The assemblage of crystal 58, insert 72, and electrode 74 is configured to nest within an insulative cup 80 formed, for example, of Teflon brand of poly(tetrafluoroethylene) or the like. Cup 80 is configured having a hole 82 at the center point thereof for the purpose of receiving wire 78 and accommodating solder bead 76. To assure removal of all ionic contaminants, cup 80, shell 66 and window 68 are boiled repeatedly in distilled water prior to assembly.

Cup 80 and its internested components are slideably retained within a cylindrical cavity 84 bored within a slug or blocking component 86. Formed having a principal diameter which is slideable within the tube 66, the slug 86 is fashioned of copper or tungsten or the like and functions both to provide a secure support for the crystal mounting components and to assure radiation blockage with respect to any radiation impinging from the rearward portion of the probe 12. Component 86 is counterbored at 88 to accommodate for the solder bead 76 upon assembly. Communicating from counterbore 88 is a bore 90 of small diameter selected to receive the small wire 78 which extends to an electrical connector 92. Connector 92 is covered with an electrically insulated material and is slideably inserted into bore 90, the outer head portion thereof at 94 residing with a counterbore 96 within component 86. Blocking or backing component 86 additionally is configured having a coupling portion of lesser outer diameter 98 which is configured to be slideably received within the internal diameter of a supporting tubular portion 100. The forwardly disposed tubular region of portion 100 at 102 is configured having a diameter to, in turn, coincide with that of the main diametric component of slug 86 so to slideably receive tubular portion 66 upon assembly. Upon such assembly, as shown in FIG. 2, an additional retainer groove as at 104 is developed. For assembly, additionally, a connector wire as at 106 provides electrical connection between connector 92 and the preamplifier 44 (FIG. 2).

The sub-assemblage of electrode 74, cup 80 and slug component 86 along with connector 92 is provided prior to a final combination of the forward probe part. In this regard, it is desired that the wire 78 be maintained in tension to assure no mechanical movement in the sub-assembly. To provide this, the wire is coupled to the connector 92 and supported so as to extend through bore 80 and into contact with the solder bead 76 within the cup 80. Cup 80 will have been positioned along with the electrode 74 within cavity 84. The disk electrode 74 then is heated such that a sweat soldering of the wire takes place and connection is made with the components in a heated state. Upon cooling, the resultant assemblage provides for the wire remaining in tension to secure against component motion. An avoidance of any relative motion of the components is important because of the capacitive effect developed with any relative motion between the components of the assemblage. The noted sub-assemblage along with the remaining components described in connection with FIG. 3 then are "slid" together under a dry nitrogen atmosphere.

Looking to FIG. 4, the components shown in expanded form in FIG. 3 are represented in their post-assembly orientations. Note that the foamaceous insert 68 has been compressed to aid in securing the remaining components from any motion. The foam material is compliant in this regard to assure a uniform compression of all components into the crystal 58. Similarly, the slightly adhesive and compliant silicon rubber inserts 62 and 72 aid in this securement. Components 100 and 66 may be retained together, for example, using an epoxy adhesive. As noted earlier, the mildest of vibrational movement may create a capacitive alteration on the order of a gamma strike for the very delicate instrument. Thus, the arrangement shown serves to provide mechanical securement. There also is a potential for vibration and the noise difficulties that ensue due to the microphonic effects occasioned by the occurrence of noise of the mildest of disturbance at the window 18. Foamaceous material 68, as well as the inserts as at 70 provide a protection for such effect due to the change of acoustic impedance. For example, any microphonic effects at the window surface 18 will be damped by the change of acoustic impedance at the junction between window 18 and foamaceous material 68. A similar alteration occurs between the insert 68 and the next subsequent silicon rubber insert 70. This alteration of acoustic impedance is analogous to the difficulties in vocally communicating from the atmosphere to a listening positon beneath the surface of water. Generally, the principal source of microphonics effects is occasioned with rubbing at the surface of window 18, a condition to be encountered in normal operations. Of course the maintaining of tubular portion 66 and the entire housing of the probe including compoents 100 and handle 22 at ground reference functions to provide an electrical shielding. It has been found helpful to dampen acoustic vibration of window 18 by applying a polymeric coating to its outside or inside surface, i.e. Teflon or the like.

Referring to FIG. 4A, an alternate and effective arrangement of the forward portion 20 of the instrument 12 is portrayed in similar fashion as FIG. 4. In the figure, a disk of the earlier-described electrically conductive silicon rubber 71 is positioned against the inner surface of window 18. The opposite face of this insert 71 then confronts a dead air space 73 which, in turn, extends to an assemblage comprising the earlier-described electrically conductive foamaceous material 68, rubber insert 70 and crystal 58. These components are retained compressively together by a band 75 which is structured of a material permitting the transmission of gamma radiation therethrough but which, preferably, additionally is electrically conductive. Aluminum, for example, may be used for the band 75. The remainder of the structure is identical with the structure of FIG. 4 as labelled with the same numeration. Providing a uniform resistance from the forward surface of crystal 58 to ground in an important aspect of each of the embodiments shown in FIGS. 4 and 4a.

As represented at circuit board 44 in FIG. 2, in order to carry out the treatment of the very faint charges which are evolved due to gamma interaction with crystal 58, it is important that the preamplification function take place as close as possible to the situs of the interaction. Because of the operational need in surgery for the 30° cant of the central axis of the forward portion 20 with respect to the corresponding axis of the rearward support portion 22 of the probe 12, some small lenght of transmission wire as at 106 is required. Because extremely small charges of current are involved in the range of 300-600 atto coulombs, a preamplification stage which performs to achieve a very high gain is called upon but one which performs with low noise generation. In effect, the preamplification stage of the instant apparatus is one achieving a voltage amplification, for example on the order of about 25,000. Correspondingly, if one considers the current amplification function numbers of electrons constituting very faint charges are converted to about a milliampere at the output of the preamplification stage, an enormous gain condition (about three trillion). The resultant power gain is about $8 \times 10^{16}$.

Figure 5:
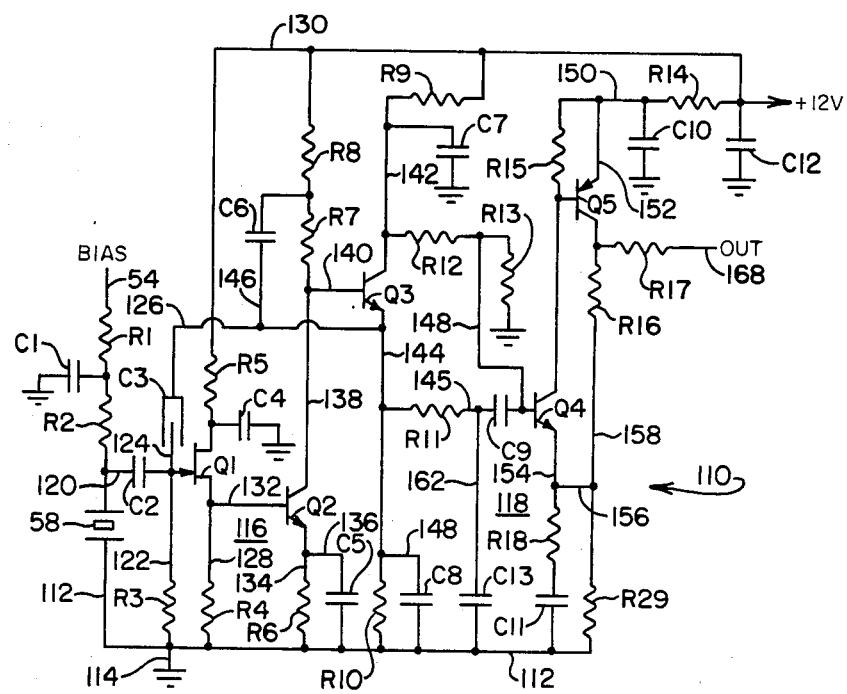
FIG. 5 is an electrical schematic diagram of a preamplifier incorporated within the instrument of FIG. 3.

Looking to FIG. 5, a preamplifier circuit represented generally at 110 employed with the instrument 12 is revealed. In the figure, earlier described input line 54, carrying the bias for assertion at the rearward face of crystal 58 again is reproduced as extending to one side of crystal 58 through resistors R1 and R2. Resistor R1 in combination with a capacitor C1 provides a local filter to remove any spurious noise which may be engendered in the line transmitting the noted bias signal. The opposite face of crystal 58 is coupled to ground as represented at lines 112 and 114. In general, the preamplifier circuit 110 includes an integrator stage represented generally at 116 which is followed by a voltage amplification and line driver stage represented generally at 118. Integration stage 116 is formed of three transistors identified at Q1-Q3 performing in conjunction with a capacitor C3.

The input to stage 116 from crystal 58 includes a crystal bias resistor R2 of very large resistance value, for example about 50 megohms, a level selected to avoid absorbing current disturbances from crystal 58. Generally, the resistance for this component will be selected between about 10 to 200 megohms. The input signal to the integration stage 116 at line 120, typically about 300-600 atto coulombs, is asserted through coupling capacitor C2 to the gate input terminal of an N-channel junction field effect transistor (JFET) transistor Q1. Line 120 also is coupled via line 122 and bias resistor R3 to ground at line 112. The resistance value at resistor R3 is selected commensurately with the selection of resistance for resistor R2, preferably at about 200 megohms to avoid signal absorption. Generally, the resistance for this component will be selected between about 10 to 10,000 megohms, the component supplying bias for transistor Q1. Also extending from line 120 at the input to the integrator stage is line 124 leading to a coaxial capacitor C3, the opposite side of which is coupled to integrator stage feedback line 126. Capacitor C3 is very small, typically having a capacitance of 0.25 picofarads and, in general, having a capacitance less than one picofarad. To create this capacitor C3, copper tubing having a 0.050 in. outside diameter is employed in conjunction with an insulated wire inserted in its center. Wire 126 is soldered to close the opposite side of the tube. Thus, by moving wire 124 inwardly and outwardly of the surrounding tube coupled to wire 126, the capacitive value at capacitor C3 may be altered. Capacitor C3 may be tuned in the above manner to adjust the preamplification stage 110 for gain. Such construction of capacitor C3 may be referred to as "coaxial".

JFET transistor Q1 functions, in effect, as a "source follower" charge amplifier, its purpose being to achieve an impedance transformation from a very high impedance gate suited to low current and low noise. In general, the JFET structure exhibits lowest current noise at the room temperature operating conditions contemplated for the instant instrument. Further, these devices exhibit high frequency response (wide bandwidth) as well as a high amplification factor or high transconductance. In view of the latter aspect, the device tends to create a large current disturbance at its source terminal at line 128. Line 128 extends through a source load resistor R4 to ground line 112. The resistor R4 functions as a d.c. current return device. The drain terminal of transistor Q1 is coupled to +12 v supply via line 130, while the same terminal is decoupled or isolated by a filter comprised of capacitor C4 and resistor R5 connected with line 130.

The signal related voltage at line 128 is coupled via line 132 to the base of NPN, bi-polar transistor Q2. Transistor Q2 performs a voltage amplification and a singular bi-polar component is elected for this function inasmuch as such devices exhibit low voltage noise characteristics at room temperatures. Additionally, the devices have a higher amplification factor availability than corresponding field effect transistors. The use of such a bi-polar device in conjunction with the input field JFET device was evolved following significant experimentation and represents a lowest noise combination which was achieved in conjunction with room temperature operation.

The degree of amplification achievable with the stage Q2 is related to the impedance exhibited with respect to its emitter and collector, i.e. the value of the collector load impedance divided by the emitter impedance. In the arrangement shown, the emitter of transistor Q2 is coupled via line 134 to ground through resistor R6 and, importantly, the emitter is by-passed to ground via lines 134 and 136 through capacitor C5. The latter component exhibits relatively low impedance on the order of 25 ohms at the frequencies of interest. Looking to the collector to supply arrangement at line 138, there is a relatively high resistance value resistor R7, for example of 3 Kohms and, in series, a resistor R8 having a 1.5 Kohms resistance to provide a total resistance of 4.5 Kohms. To achieve the most effective amplification or highest gain, NPN transistor Q3 is so coupled within the integrator stage 116 as to provide a "boot strap" circuit to raise the effective collector impedance to transistor Q2. In this regard, the base of transistor Q3 is coupled via line 140 to line 138, while the collector thereof at line 142 is coupled to supply line 130 in conjunction with a decoupling filter comprised of resistor R9 and capacitor C7. The emitter of transistor Q3 is coupled to line 126 as well as to line 144 to ground through resistor R10. Line 126 is seen to extend to line 146 incorporating capacitor C6 and coupled intermediate resistors R7 and R8. Transistor stage Q3 functions as an emitter follower, feeding the noted junction between resistors R7 and R8 through capacitor C6 in boot-strapping fashion. The result is to raise the effective impedance at the collector of transistor Q2 due to the alteration of net current flow through resistor R7. This provides a much higher voltage gain achieved at the integrator stage 116. Note that a portion of the signal from the emitter of transistor Q3 returns to the coaxial capacitor C3 of the integrator stage.

Voltage amplifier and line driver stage 118 is seen to be comprised of an a.c. voltage amplifier configured as the combination of NPN transistor Q4 and PNP transistor Q5. Such an arrangement comprises desirably few components and exhibits high gain and very broad bandwidth. Because the gamma ray interaction of crystal 58 will exhibit a frequency disturbance spectrum ranging from about 50 KHz to 200 KHz the frequency response of the stage 118 is tailored accordingly. For example, the high end roll off of this response is established by resistor R10 within line 144 and capacitor C8 within line 148. The output of the integrator stage is asserted through resistor R11 and capacitor C9 to the base of transistor Q4. A voltage bias to the base of transistor Q4 is provided via line 148 from supply following its division by divider resistors R12 and R13. This bias input, amounting to about one-fourth of the supply voltage also is treated by the filter combination of resistor R9 and capacitor C7.

The 12 v power supply additionally is filtered by a pi filter comprised of capacitors C10 and C12 along with resistor R14 connected within line 150. Line 150, in turn, is seen to extend via line 152 to the emitter of transistor Q5 and through resistor R15 to the base thereof as well as to the collector of transistor Q4. Correspondingly, the emitter of transistor Q4 extends via lines 154, 156 and 158 to resistor R16 and the collector of transistor Q5 as well as to resistor R29. The output of stage 118 is provided at line 168 incorporating resistor R17. The gain of this output stage is set by resistor R18 within line 154 in conjunction with resistor R16, while capacitor C11 in that line aids in the setting of low frequency roll-off of the stage. The high frequency roll-off characteristic is further aided by the combination of resistor R11 and capacitor C13, the latter component being coupled between line 145 and ground via line 162. Low end roll-off characteristics for the stage further are aided by the combination of capacitor C5 and resistor R6.

Figure 6:
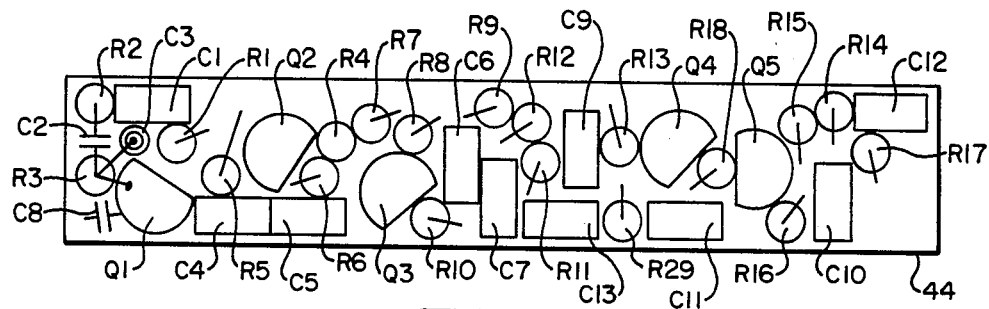
FIG. 6 is a layout drawing of the component positioning on a circuit board implementing the circuit of FIG. 5.

In view of the extreme sensitivity of the type of preamplifier at hand and the tendency of such circuitry to oscillate, the layout of the circuit within housing portion 22, for example on a circuit board as at 44, also becomes an important aspect in the design of the instrument. Thus, looking to FIG. 6, a layout for the preamplifier circuit showing component orientations and relative positioning is revealed. In general, the most sensitive components are grouped to the left in the figure, a position corresponding with a left orientation in conjunction with FIG. 2. As a consequence, these components are closest to the crystal in the system. Because of the very large resistance values for resistors R2 and R3, these resistors are to the left in the circuit orientation and are mounted vertically upwardly from the board or base, one side of them being attached at such base. The opposite sides of these resistors extend in space to couple to capacitor C2. Thus, capacitor C2 is off the surface of the printed circuit board to avoid leakage conditions. The most sensitive transistor in the system is JFET transistor Q1 whose source and drain terminals are coupled to the printed circuit board, while its gate electrode extends to the common junction in space of capacitor C2 and the resistor R3. Thus, this sensitive terminal also resides in space in close proximity to the crystal itself. Coaxial capacitor C3 is mounted upon the board in a vertical orientation such that its tuning wire line 124 is coupled from its coaxial location within the component to the common juncture of the gate of transistor Q1 and the upstanding common junction of resistor R3. The above-described are the most sensitive of the components and their mounting in the manner shown has been found to be important to successful operation of the device. Capacitor C18 is a radial-lead device and is seen coupled to the left side of the circuit board for convenience as may be observed by looking to its corresponding position in FIG. 5. Note that the component developing the highest amplification effect, transistor Q5, is furthest to the right on the circuit board away from the sensitive gate at transistor Q1. The remaining components are shown in their orientations on the circuit board 44 along with small lines representing the "hair pin" type mounting orientations.

Figure 7A:
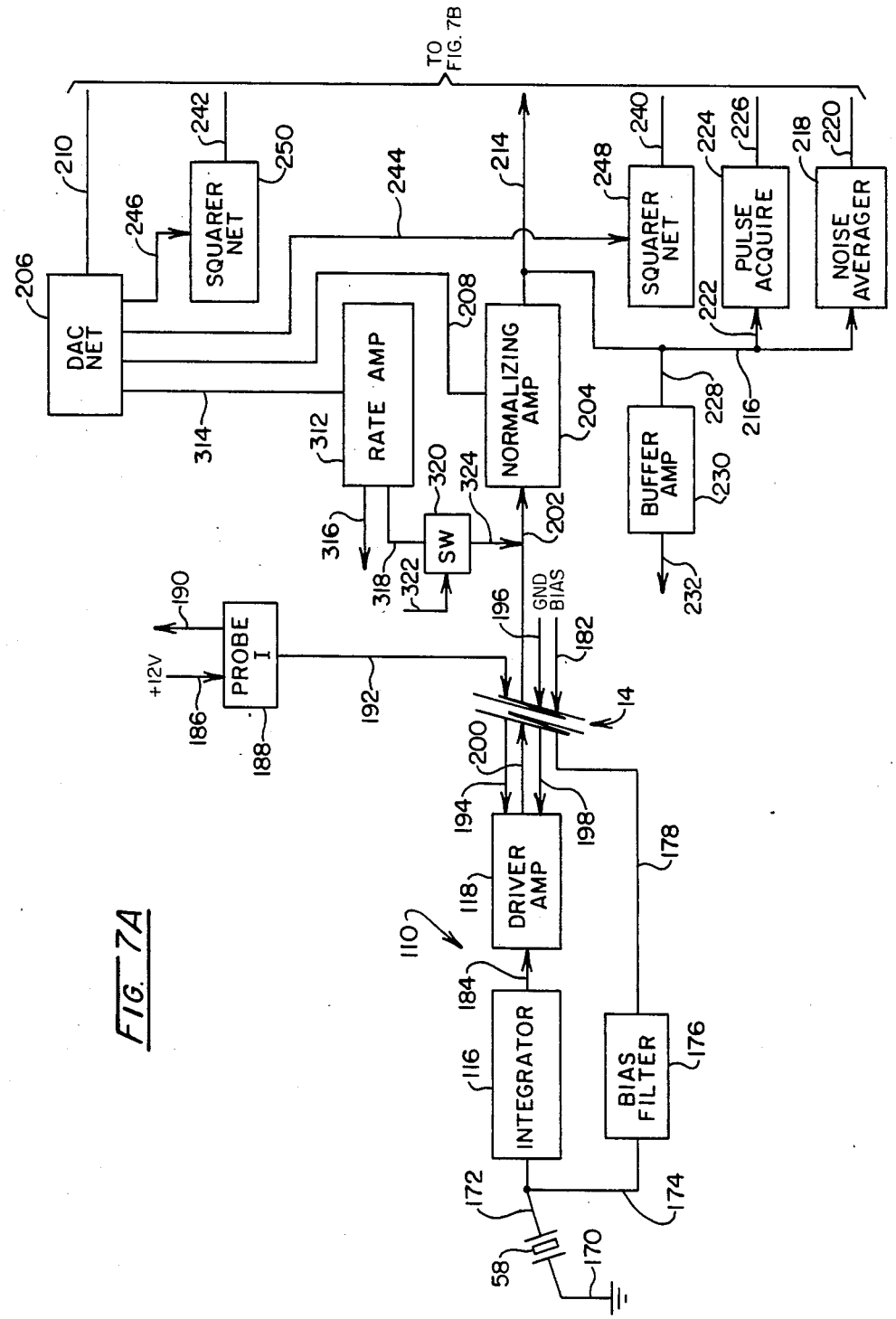

Referring to FIGS. 7A and 7B, a block diagrammatic representation of the instrumentation circuitry is revealed. In FIG. 7A, the cadmium telluride crystal 58 again is shown having one face coupled to ground through line 170, while the opposite, biased face thereof is coupled via lines 172 and 174 to a bias filter represented at block 176. As noted above, this filter, for example, includes resistor R2 as well as capacitor C1 and resistor R1. The input to the filter components 176 is represented at line 178 as being applied through the triaxial cable as described earlier at 14 and represented by that numeral herein. Line 178 corresponds with the earlier-described line 52 in FIG. 2. This bias emanates from a power supply shown at block 180 in FIG. 7B and represented at line 182.

Line 172 from the crystal 58 is shown extending to the earlier-described integrator stage of the preamplifier 110. The integrated valuation of detected radiation disturbance then is shown directed, as represented by line 184, to the driver-amplification network described generally at 118 in FIG. 5 and identified by that numeration in block form in FIG. 7A. A 12 v power supply is provided from the power supply 180 (FIG. 7B) as represented at line 186 which, as shown in FIG. 7A, is directed to a probe current network represented by block 188. Under microcomputer control as represented by line 190, the network 188 develops signals, for example, determining whether the probe instrument 12 has been properly connected to the console 16. Delivery of the 12 v power supply for the preamplifier stage 110 is represented at line 192 as extending to the driver amplifier from cable 14 via line 194. Line 194 corresponds with the clad 46 described in conjunction with cable 14 in FIG. 2.

Ground to the instrument 12 also is developed from the power supply block 180 as represented at line 196 shown in FIG. 7A as extending to cable 14 and via line 198 to the instrument and preamplification components 110. Line 198 corresponds with the earlier-described clad at 48 in FIG. 2.

The output of the preamplification circuit 110 is represented at line 200 extending through the cable representation 14 corresponding with the earlier-described line 54 in FIG. 2. Line 200 extends from the cable 14 as line 202 to the input of a normalizing amplifier represented at block 204. The network represented by block 204 functions to amplify or attenuate, i.e. scale the noise characteristic of any given instrument 12 and normalize the value thereof or render it consistent for later comparison stages. Generally, for example, the 27 kev energy level gamma ray generated pulses in the system will be about five times higher than noise levels. Normalizing amplifier network 204 will establish those noise levels at some predetermined level, for example, 200 millivolts and the resultant proportional valid gamma related pulses will become about one volt high for purposes of ensuing comparison functions. It may be observed that the amplifier network at block 204 is shown controlled from a digital-to-analog converter network represented at block 206 via line 208. Network 206, in turn, is controlled from line 210 extending, as shown in FIG. 7B to block 212 representing a microcomputer network. The normalized output developed from network 204 is presented along lines 214 and 216 to a noise averager circuit as represented at block 218. This network, represented at block 218 determines an average amplitude value for the noise of a given system with a given instrument 12 and provides a corresponding signal as represented at line 220 (noise amp) which is employed as above-described as information used by the microcomputer 212. This information in addition to being employed with the normalizing amplifier network represented at block 204, may be employed to develop a low window valuation for the comparison function.

Line 216 also extends via line 222 to a pulse acquire network represented at block 224. This network functions, when activated by the microcomputer represented at block 212, to acquire the value of the highest pulse amplitude witnessed at line 222. Periodically, this information then is transmitted to the microcomputer at block 212 as represented by line 226. Representing a form of peak detector, the network is sometimes referred to as a "snapshot circuit". Also produced from line 216, as at line 228 and block 230 is a buffer amplifier which will provide at line 232 an output representing received pulses which may be made available at the rearward portion of console 16 for conventional radiation evaluation purposes.

Line 214 extends, as shown in FIG. 7B at line 234, to one input of an upper window comparator represented at block 236 and a lower window comparator illustrated at block 238. The threshold levels for comparative purposes employed by the network at block 238 is shown asserted from line 240 and, preferably, is developed by the logic of microcomputer network 212 at a level just above the noise amplitude signals generated from line 220. Of course, manual setting of such windows can be carried out. In similar fashion, the upper window of acceptance for valid gamma ray interaction is established from a corresponding line 242. This threshold setting may be made from the information taken from pulse acquire network 224.

Returning to FIG. 7A, the threshold upper window and lower window threshold selections are made under the control of the microcomputer network at block 212 as controlled from the digital-to-analog network shown at block 206. It is the characteristic of such networks as at block 206 to provide an output which is comprised, for example, of 256 steps of varying amplitude. The percentage of incrementation from step-to-step will vary somewhat over the range of voltage values provided. Accordingly, the outputs from this conversion network at block 206, as at lines 244 and 246 are directed to squarer networks shown, respectively, at blocks 248 and 250. These networks function to square the current outputs at lines 244 and 246 and thus achieve a uniform percentage incrementation of the threshold defining outputs at lines 240 and 242.

Returning to FIG. 7B, the outputs of the comparator networks shown at blocks 236 and 238 represent candidate pulses which may be above or below the given thresholds and are identified as being presented as a "UW pulse" and an "LW pulse" along respective lines 256 and 258. These lines are shown directed to a real time pulse discriminator network represented at block 260 which carries out Boolean logic to determine the presence or absence of valid pulses. Valid pulses are introduced to the microcomputer network 212 as represented by line 262.

The microcomputer represented at block 212 performs under a number of operational modes to provide both audio and visual outputs to aid the surgeon in locating and differentiating tumorous tissue. In the former regard, as represented at line 264 and block 266, a volume control function may be asserted with amplitude variations controlled from a solid-state form of potentiometer as represented at line 268 and block 270. Further, a "siren" type of frequency variation may be asserted as represented at line 272 to an audio amplification circuit represented at block 274 for driving a speaker as represented at 276 and line 278. With the noted siren arrangement, the frequency output from speaker 276 increases as the instrument 12 is moved closer to the situs of concentrated radiation. Of course, conventional clicks and beeps can be provided at the option of the operator.

The microcomputer network 212, as represented by arrow 274 and block 276 also addresses an input-output network which, as represented at arrow 278, functions to provide a pulse count output of varying types as well as outputs representing volume levels, pulse height, noise levels and battery status. Visual readout is represented in FIG. 7B as a block with the same display 26 numeration as described in conjunction with FIG. 1. Similarly, the input-output function represented at block 276 provides appropriate scanning of the keyboard or switches described in conjunction with FIG. 1 at 30 and represented by the same numeration in FIG. 7B. During a counting operation, the microcomputer network 212 functions to control a light emitting diode drive network represented by block 282 from line 284. The drive network represented at block 282 is shown providing an input, as represented by line 286 to the dual LED display as described at 28 in FIG. 1 and represented in block form with the same numeration. This readout provides a red light when a gamma ray is detected and a green light during the counting procedure in general. A serial output port of conventional variety also is provided on the console 16, such ports being represented at block 288 being addressed from the microcomputer at block 212 from line 290 and having output and input components represented by arrow 292. A real time clock-calender having a non-volatile memory also may be provided in conjunction with the functions of the microcomputer network 212 as represented by block 294 and arrow 296. Further, the microcomputer may be employed to monitor the performance of the power supply represented at block 180. This is shown being carried out by the interaction of the microcomputer network with a multiplexer represented at block 298 and having an association represented by arrows 300 and 302. It may be observed that the power supply also provides +5 sources for the logic level components of the circuit as represented by line 304; a −5 v source at line 306, as well as a −9 v reference at line 308 for display 26 drive and, finally, a 2.5 v reference as represented at line 310 to provide reference input to the analog circuitry described later herein.

Returning to FIG. 7A, the microcomputer network as represented at block 212 also provides an input to the digital-to-analog conversion network represented at block 206 which corresponds with the instantaneous pulse rate and this information is conveyed to a pulse rate amplifier network represented at block 312 via line 314. The resultant output as represented at line 316 may be provided, for example, at the rear of the console 16. This circuit represented at block 312 also may be employed to generate a calibrating pulse for testing the downstream components of the system. Thus, the microcomputer applies a predetermined pulse level through the digital-to-analog conversion network at block 206 for presentation to the amplifier network represented at block 312. The resultant output at line 318 is selectively switched as represented by block 320 to define pulse width from the microcomputer input in line 322 to generate the calibrating pulse at line 324.

Figure 8B:
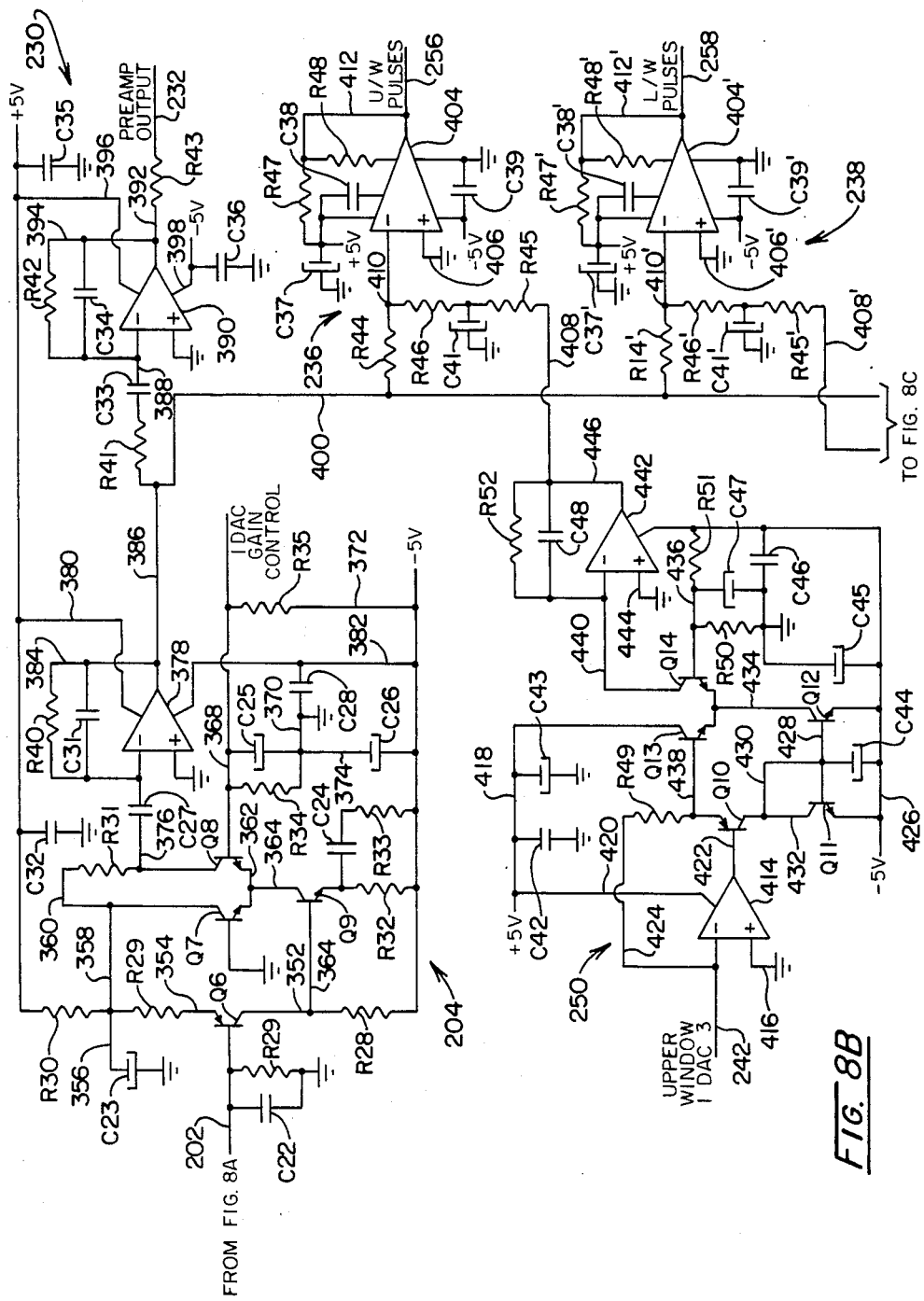
Figure 8C:
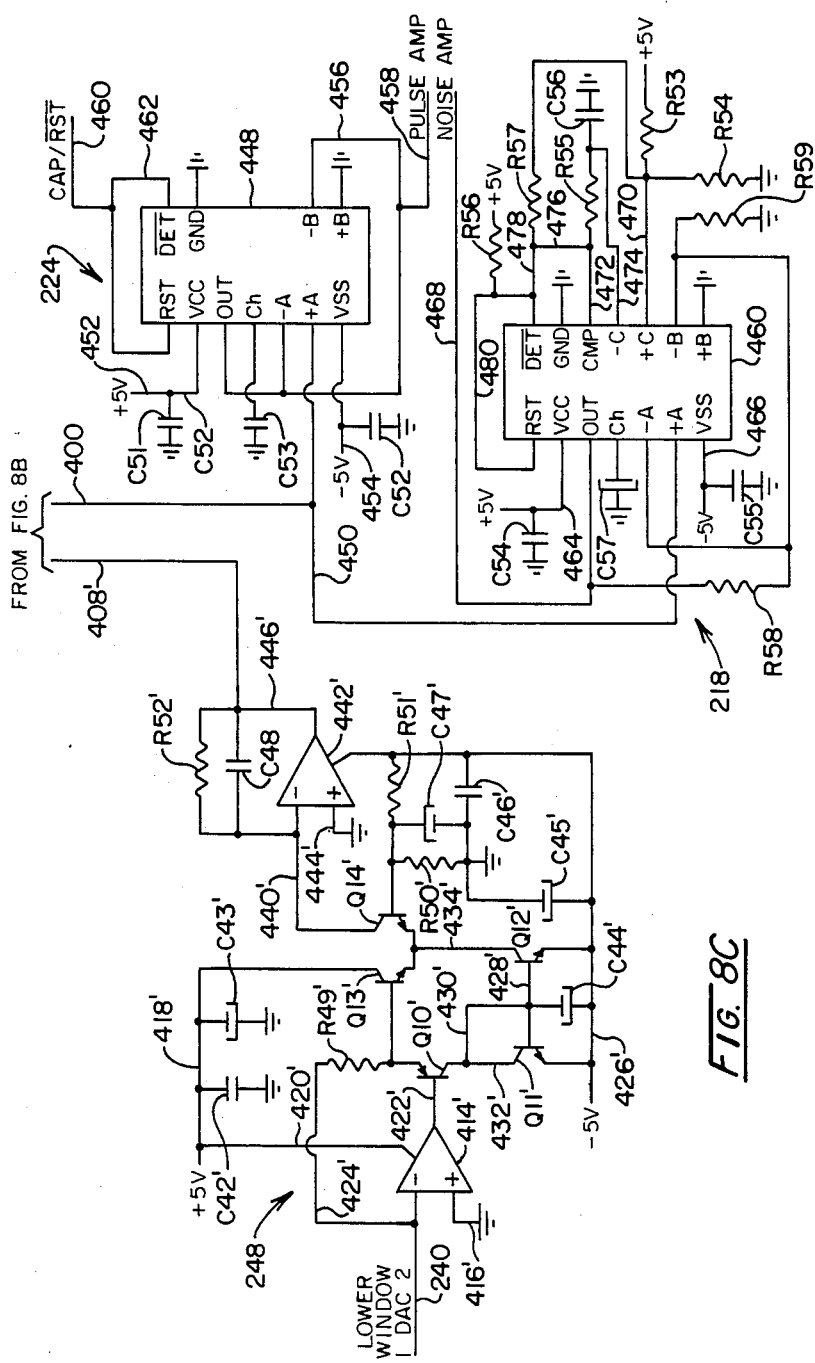

Referring to FIGS. 8A-8C, pulse treating analog circuits as are maintained in console 16 are revealed. In FIG. 8A, the output of a 10 pin ribbon cable which, in turn, is coupled to triaxial cable 14 is revealed generally at 330. Of the ten connecting pins and lines of this ribbon cable, five are at ground for shielding purposes as represented by ground line 332. The bias supply is provided from the earlier-described power supply as at block 180 and shown again at line 182 extending through resistor R20. Correspondingly, the +12 v power supply earlier described at line 186 again is reproduced as extending to the terminal 330 through resistor R21. Lines 182 and 186 are seen coupled to respective filtering capacitors C16 and C17. Finally, the preamplified detector pulse output is received from the connector 330 from along line 332 and is applied to the analog downstream circuitry through blocking capacitor C18.

The probe current detector described earlier in conjunction with block 188 in FIG. 7A again is represented in general by that numeral in FIG. 8A. This detector employs resistor R21 within +12 v supply line 186. The opposite sides of resistor R4 are tapped at lines 334 and 336 which, in turn, are directed to a resistor network comprised of resistors R22-R25 and thence are directed to the inputs of an operational amplifier 338. A filtering capacitor C19 additionally is coupled to one side of resistor R21. The resistor network R22-R25 and amplifier 338 form an instrumentation amplifier which measures the voltage difference across resistor R21 and further functions to perform a level shift of 12 v to ground. Following such level shifting, the resulting probe current responsive signal at line 340 is directed to the non-inverting input of a second amplification stage 342. Stages 338 and 342 are shown coupled to +12 v as filtered by capacitor C20 via line 344 and to −12 v supply as filtered by capacitor C21 via line 346. The inverting input to amplifier 342 at line 348 incorporates resistor R26 and, additionally is coupled to the output of stage 342 at line 350 via resistor R27. Amplification stage 342 functions to amplify the signal from stage 338 by a factor, for example, of 10 to provide an analog signal representative of probe current (PROBE I) at line 352. This analog signal is directed to the microcomputer function earlier described at block 212 in FIG. 7B.

Line 202, carrying the preamplified gamma reaction pulses is directed, as shown in FIG. 8B, to the input of the normalizing amplifier network represented in FIG. 7A at block 204 and shown in general by that numeration. The signal at line 202 is filtered by a capacitor C22 while a resistor R27 supplies bias to PNP transistor Q6. These filter components provide a high frequency roll-off avoiding RF interference which may be encountered. The collector of transistor Q6 is coupled via line 352 and resistor R28 to −5 v supply, while the emitter thereof at line 354 is coupled through resistors R29 and R30 to +5 v supply. Resistor R30 provides a supply bypass filter function in conjunction with a capacitor C23 coupled with line 354 via line 356, while resistor R29 provides emitter bias for transistor Q6. Further filtering for line 356 is provided by capacitor C23. This relatively stable supply at line 356 is directed via line 358 to line 360 extending in one direction to the collector of NPN transistor Q7 and in the opposite direction through collector load resistor R31 to the collector of NPN transistor Q8. Transistors Q7 and Q8 are coupled as a differential pair, having a common emitter connection at line 362 which extends via line 364 to the collector of NPN transistor Q9. The base of transistor Q9 is coupled by line 364 to line 352, while the emitter thereof is coupled via resistor R32 to −5 v. The high pass filter comprised of capacitor C24 and resistor R33 additionally is coupled from the emitter of transistor Q9 to −5 v.

The base of transistor Q7 is coupled to ground via line 366, while the corresponding base of opposite transistor Q8 is coupled via line 368 to the digital-to-analog control described in connection with block 206 in FIG. 7A. Line 368 will receive a controlling current as directed by the microcomputer network 212 to carry out a normalization process. Line 368 additionally is coupled with a voltage dividing network comprised of resistors R34 and R35, the former resistor being positioned within line 370 and the latter within line 372. Note that line 370 is directed to ground. As a consequence, a slight bias voltage is applied to the base of transistor Q8 as is further filtered by capacitor C25. Capacitor C26 within line 374 functions to filter ground line 370 from −5 v supply.

The collector of transistor Q8 is coupled via line 376 and coupling capacitor C27 to the inverting input of an operational amplifier 378. The non-inverting terminal of the amplifier is coupled to ground, while power input to the device 378 is developed from +5 v supply via line 380 and from −5 v supply via line 382. A capacitor C28 filters the latter line. The gain set and high frequency roll-off characteristic of amplification stage 378 are derived by the feedback path shown at line 384 incorporating resistor R40 and capacitor C31 to provide an output at line 386. With the arrangement shown, the a.c. signal applied to the base of transistor Q6 becomes a fluctuating current at its collector which is referenced against −5 v supply. There develops in consequence an a.c. signal across transistor Q9 which creates a.c. current in its collector. That a.c. current is split along two paths associated with differential transistors Q7 and Q8. By controlling the current input from the digital-to-analog converter at line 368, the d.c. voltage at the base of transistor Q8 may vary above or below ground. Where it varies below ground, the a.c. signal into the collector of transistor Q8 is diminished and, conversely, if that value is above ground the current is starved from the collector of transistor Q7 and accentuated at transistor Q8. Operational amplifier 378 buffers the resultant signal conditioning and applies it as raw pulse data to line 386. In operation, the microcomputer function described in conjunction with block 212, evaluates the noise amplitude at line 220 (FIG. 7B) and adjusts the signal at line 368 such that the noise condition achieves a nominal consistent value, notwithstanding that different probe instruments as at 12 may be employed. This assures performance at the upper and lower window comparator functions described in conjunction with blocks 236 and 238 in FIG. 7B which is consistent and proper from probe-to-probe.

The raw pulses at line 386 are directed, inter alia, through frequency shaping elements including resistor R41 and capacitor C33 in line 388 to a buffer stage described in conjunction with block 230 in FIG. 7A which is formed of an operational amplifier 390. The non-inverting input of the amplifier is coupled to ground while additional frequency shaping in gain elements thereof are provided in feedback fashion from the output line 392 of the amplifier via line 394 to line 388. This feedback path incorporates resistor R42 and capacitor C34. The amplifier stage 390 is powered from +5 v via line 396 coupled to +5 v which is filtered by capacitor C35 and is coupled to −5 v supply from line 398 which is filtered by capacitor C36. The resultant output, as presented through resistor R43, may be employed for peripheral devices such as oscilloscopes and the like wherein the buffered raw pulse data may be analyzed.

Line 386 extends additionally via line 400 to the input of comparator stages described in conjunction with blocks 236 and 238 in FIG. 7B and identified in general by the same numeration in FIG. 8B. These stages are essentially identically structured and thus, identical numeration is employed in their description but with primed notation in conjunction with the circuit at 238.

The comparator stage 236 is formed of a type LT1011CN8 comparator as at 404 into which the negative going raw pulse data from line 400 is asserted through a resistor R44 to the inverting input. Note that the non-inverting input terminal of the comparator is coupled to ground via line 406 and is thus at 0 volts. As a consequence, the assertion of signals more positive than 0 voltage on the inverting input will cause the output at line 256 to assume a low value, and signals more negative than 0 on this inverting input will cause the output at line 256 to transition to higher value. The reference signals which are applied to stage 236 are presented from line 408 and extend through resistors R45 and R46 to the inverting input to create a current to the input of the system that is essentially balanced by the current from raw pulses at line 400. Any time these currents sum at point 410 to a voltage more negative than 0, a positive pulse will be outputted from the comparator 404. This arrangement is provided, inasmuch as comparators perform more effectively where a small common mode range is involved. Capacitor C37 of the stage provides a 5 v by-pass to accommodate digital noise. Resistor R47 provides a pull-up function via line 412 for the open collector output of the comparator, resistor R48 and capacitor C38 provide a hysteresis for snap action as threshold switch-over is approached by the comparator 404 and capacitor C39 provides a by-pass for the −5 v supply. Capacitor C41 provides additional filtering of the window potential from the squaring circuits 250.

As noted above, the configuration of comparator stage 238 providing an output at line 258 is identical to that of comparator stage 236 and thus its components are identified with the same numeration in primed fashion.

Now looking to the squarer circuit earlier described in conjunction with block 250 in FIG. 7A and represented in general by that numeration in FIG. 8B, a current is supplied from the digital-to-analog converter network as represented at block 206 in FIG. 7A under the control of the microcomputer function represented in FIG. 7B at block 212. This current establishes the threshold level for the operation of comparator stage 236 and is shown herein as line 242 which is directed to the inverting input of operational amplifier stage 414, the non-inverting input of which is coupled to ground via line 416. Amplifier 414 is coupled to +5 v at line 418 through line 420 and capacitors C42 and C43 coupled with the former line provide a filtering function. The output of stage 414 at line 422 is coupled to the base of PNP transistor Q10, the emitter of which is coupled through line 424, incorporating resistor R49, to the inverting input at line 242. Thus current is caused to flow from the output of the amplifier 414 through the feedback line 424 which develops a negative voltage at the lower end of resistor R49. Generally, this control current at line 242 will vary from 0 to 250 microamps and the voltage corresponding therewith across resistor R49 will vary from zero volts to −150 millivolts. The 250 microamps required at the output is derived from the negative voltage supply at line 426 coupled to transistor Q11 of a current mirror comprised of transistors Q11 and Q12 operating in conjunction with capacitor C44. In the arrangement shown, the emitters of NPN transistors Q11 and Q12 are coupled to −5 v at line 426, while their bases are in common as represented by line 428. The collector of transistor Q10 is shown coupled to line 428 via line 430, while the corresponding collectors of transistors Q10 and Q11 are coupled in common through line 432. Correspondingly, the collector of transistor Q12 is coupled via line 434 to the common emitter outputs of differential pair transistors Q13 and Q14.

In general operation, mirror structures as shown perform such that a current which flows into transistor Q11 will be split between lines 430 and 432, most of the current flowing into the collector and out of the emitter and a fraction thereof flowing into the base and out the emitter. That current which flows into the base of transistor Q11 will cause a base-to-emitter potential to be developed proportional to the currents flowing at the collector base combination, i.e. proportional to the Beta of the transistor. Transistor Q12 is identical to transistor Q11 having a common base therewith and thus the same voltage will be exhibited at the base of transistor Q12 and an identical collector current will be caused to flow. Thus, the collector current to transistor Q11 is matched by a corresponding collector current at line 434 with respect to transistor Q12 to evolve a current mirror operation. In the present configuration, current is flowing out of the collector of transistor Q12 and into the differential transistor pair Q13-Q14 common emitter junction. The base of transistor Q14 at line 436 is at a fixed voltage, for example −100 mv by the combination of resistors R50 and R51 which function to form a voltage divider between ground and −5 v supply. This permits the varying voltage (0 v to −150 mv) at the base of transistor Q13 as coupled to the emitter of transistor Q10 via line 438 to be both more positive and more negative than the base value voltage at line 436. Thus, the amount of current available at the source line 434 is changed as well as the proportion of current that flows through the transistor Q14, a capability being present to divert a greater or lesser amount of current out of the collector of transistor Q12 effecting a deviation of current from the transistor Q14. This creates an analog squaring activity. If the asserted current at line 242 is quite small, then the current reflected to line 434 would be quite small and the voltage at the base of transistor Q13 will be negative but more positive than the base of transistor Q14 which is fixed at −100 millivolts. As a consequence a small step in the output is recognized. As the input currents at line 242 elevate in value, the reflected currents at line 434 become larger and, simultaneously, transistor Q13 is more and more turned off to provide more and more available current at transistor Q14. Power supply filtering is provided by the parallel coupled capacitors C45 and C46, while the d.c. level at line 436 is filtered to assure stability by capacitor C47.

The squaring current output at the collector of transistor Q14 is directed via line 440 to the inverting input of an operational amplifier 442. The non-inverting input to the amplifier is coupled via line 444 to ground and the output thereof at line 446 is coupled to line 408 as well as through resistor R52 to input line 440. A capacitor C48 performs a filtering function. Resistor R52 develops the voltage range output for the stage 442 in correspondence with squared circuit inputs thereto. The maximum value for this output voltage will be, for example, 5 v.

Looking to FIG. 8C, the squarer circuit identified in FIG. 7A at block 248 again is represented under the same general numeration. Inasmuch as this circuit is identical to that described at 250 above, the identification of components thereof is identically presented in primed fashion. Thus, control is asserted via line 240 for the lower window as a positive-going current and the resultant squared output at line 408′ is asserted to comparator stage 238 (FIG. 8B) for summing at summing point 410′.

FIG. 8C shows the extension of line 400 carrying raw pulse data to line 450, which, in turn, is directed to the +A input terminal of a peak detector configured to derive the pulse acquire function described at block 224 in FIG. 7A and identified by the same general numeration herein. The pulse acquisition stage 224 is provided as a type PKD01FP device 448 configured by coupling to +5 v at line 452 and with −5 v at line 454. Filtering of the supplies is provided by respective capacitors C51 and C52. Capacitor C53 provides a hoold function. The output of device 448 at lines 456 and 458 will represent the last and largest peak value for a given pulse detected. Commencement of measuring of the pulse heights is controlled from the microcomputer, as represented at block 212 in FIG. 7B, by input from lines 460 and 462. These inputs selectively reset the device 448 to zero valuation to commence collecting pulse heights, as well as to capture the resultant last largest pulse height for assertion at line 458 to the microcomputer for evaluation. This evaluation may be used, for example, to establish the threshold level of the upper window comparator input at line 242 (FIG. 7B, FIG. 8B). It also provides an input to the display 26.

Line 450 additionally extends to the +A terminal of a peak detector device 460 representing the princpal component of the noise averager stage described generally at block 218 in FIG. 7A and represented in general by that numeral in the instant figure. Device 460 is coupled to +5 v from line 464 and to −5 v from line 466 which, respectively, are filtered by capacitors C54 and C55.

The device 460 continually operates to acquire and reset applied inputs to a peak detector component thereof at gates +A, −A. This oscillation is provided by the configuration of a multivibrator in conjunction with a comparator stage which is extant at terminals C+, C−, and CMP. In effect, the device functions to "dither" the applied input in an essentially imperceptible manner to establish an average noise level value at line 468. With the arrangement shown, a 2.5 v reference is established at line 470 leading to the +C input to the comparator function of device 460. This 2.5 v reference is developed by a voltage divider comprised of resistors R53 and R54 in conjunction with ground and +5 v supply. The output of the comparator is provided at line 472, the oscillatory period of which is controlled by the R-C combination of resistor R55 and capacitor C56, the common junction of which is coupled by line 474 to the −C input of the comparator function. The comparator output is seen directed via lines 476 and 478 to the DET terminal of device 460 which, in turn, is coupled to +5 v through resistor R56 as well as via line 480 to the reset input terminal. A resistor R57 provides hysteresis performance. Capacitor C57 provides an averaging function for the average noise input signal while resistors R58 and R59 provide a gain, for example, of 2 for the peak detector function at the +A, −A terminals. A buffered output is provided at line 468.

Returning to FIG. 8A, the rate amplification function as well as self-test circuit discussed in conjunction with blocks 312 and 320 in FIG. 7A are illustrated at an enhanced level of detail and identified with the same general numeration. Rate output or count rate information is derived by the microcomputer network described in conjunction with FIG. 7B at block 212 and, as described in conjunction with FIG. 7A is presented to the stage 312 via line 314 extending, in turn, from the DAC network 200. Line 314 leads to the non-inverting input of an operational amplifier 486 and the current value thereof which, for example, will range from 0 to 250 microamps is directed to a 1 Kohm resistor R60 within line 488 shown coupled to ground from line 314. The output of amplifier 486 at line 490 is directed to the base of NPN transistor Q15, the emitter of which is coupled by line 492 to ground and which incorporates gain scaling resisitors R61 and R62. The inverting input of the amplifier 486 is connected by line 494 to a position intermediate the latter resistors to carry out this function. The output from amplifier 486 will, for example, range from 0 to 2.75 v and is directed via line 496 to the non-inverting output of buffer amplifier 498, the output of which is provided at the earlier-noted line 316 (7A) incorporating resistor R63. The opposite input to buffer stage 498 is coupled to output line 316 via feedback line 500 and the resultant output of the device is shown as labelled "RATE OUT" which may be used for a variety of analysis purposes.

Collector current at transistor Q15 at line 502 leads to a current mirror comprised of transistors Q16 and Q17 having common bases as represented by line 504, which bases additionally are coupled to the collector of another PNP transistor Q8, the emitter of which is coupled to +12 v supply at line 506 as asserted through resistor R64 and line 508. As before, a line 510 extends from line 502 to line 504. With the arrangement, positive current can be produced out of transistor Q17 and into the input of the normalizing amplifier via line 202. Note that the emitters of respective transistors Q16 and Q17 are coupled to line 506 through respective balancing resistors R65 and R66 and that the supply is filtered at line 506 by capacitor C58. Resistors R65 and R66 serve to balance out any differences of performance parameters with respect to transistors Q16 and Q17.

Transistor Q8 serves the switching function for the self-test and can be turned on upon microcomputer command to sink away the available current to the base of transistors Q16 and Q17. In this regard, the base of transistor Q8 is coupled via line 512 to the collector of NPN transistor Q9. Line 512 is coupled to plus supply at line 506 through resistor R67. The pulse amplitude for this simulated pulse is developed by adjusting the voltage across resistors R61 and R62 to scale the resulting current from transistor Q17. Then, upon quite rapid command, as a matter of nanoseconds, transistor Q8 can be turned off and on to enable transistor Q17 and produce the resultant pulse, the combined control, in effect, making the pulse any width and height desired for a testing procedure. The microcomputer function will produce levels on the order of 0 to 5 v into line 322. These pulses are level shifted to operate in conjunction with the +12 v supply at line 506 by NPN transistor Q19, the collector of which is coupled to line 512 and the emitter of which is coupled to line 322 via resistor R68. Two and one-half volts are applied to its base from divider resistors R69 and R70, the former being coupled to +5 v supply and the latter being coupled to ground.

Turning to FIG. 9, the volume control and audio amplifier stage described in conjunction with respective blocks 266 and 274 in FIG. 7B are represented in enhanced levels of detail along with general identification with the same numeration.

The microcomputer described in conjunction with block 212 in FIG. 7B will develop a volume output signal ranging from +5 v to −5 v through a solid-state form of potentiometer as described in conjunction with block 270 of the latter figure. This signal is applied, as earlier described, via line 268 through scaling resistor R73 to a current mirror comprised of NPN transistors Q20 and Q21. As before, the emitters of these transistors are coupled in common to −5 v supply at line 514, while their bases are in common as represented by line 516. A filtering capacitor C59 provides stability at the common bases of these transistors while a current splitting line 518 is coupled between the collector and base of transistor Q20. The output of the current mirror at the collector of transistor Q21 at line 520 is connected to the common emitter connection of differential paired transistors Q22 and Q23. The base transistor Q23 is coupled to ground through resistor R74, while the corresponding base of transistor Q22 at line 522 is modulated by an audio squarewave of controlled, variable frequency generated from the microcomputer function at block 212 and presented along line 264 through coupling capacitor C60 and resistor R75. Line 522 is seen to extend to ground through resistor R76. Thus, modulation of the current mirror controlled volume signals is provided. In this regard, the collector of transistor Q23 is coupled to +12 v and the resultant volume controlling signal generated through resistor R77. Correspondingly, the 180° phase separated equivalent signal at the collector of transistor Q22 is provided at line 526 and is provided as the opposite drive control input at resistor R78. These differential inputs are used in a push-pull drive arrangement of the audio amplification stage shown generally at 274. Looking to one side, it may be observed that the signal at line 524 is coupled to the inverting input of operational amplifier 528 through line 530 and coupling capacitor C61. The opposite input to the amplifier 528 is coupled via line 532 and resistor R79 in line 534 to ground as part of a voltage divider network including resistor R82 and capacitor C64. Amplifier 528 functions to operate respective PNP and NPN power transistors Q24 and Q25 in classic push-pull fashion. In this regard, the bases of these transistors are coupled to the output at line 536 of amplifier 528 via feedback line 538 incorporating resistor R79 and line 540. The collector of transistor Q24 is coupled to +12 v at line 542, while the emitters thereof are connected by line 544 to output line 536. The collector of transistor Q25 is coupled to ground. Line 536 is shown to incorporate resistor R80 which, in turn, is coupled to line 544. The output of the drive transistor is coupled via line 546 to one input of the loudspeaker or annunciator 276.

The corresponding differential drive signal is presented through resistor R78 and capacitor C63 within line 548 to the inverting input of operational amplifier 550. The non-inverting input to amplifier 550 is coupled to line 532 which, in turn, is coupled through resistor R80 to +12 v supply. The output of amplifier 550 at line 552 extends through resistor R81 to line 554 commonly coupling the emitters of respective NPN and PNP power transistors Q26 and Q27. Transistor Q27's collector is coupled to ground, while the corresponding collector of transistor Q26 is coupled to line 542. The output of amplifier 550 at line 552 is coupled to feedback line 556 incorporating resistor R83 and, the arrangement functions to provide push-pull or differential power to the loudspeaker 276 through coupling capacitor C65 and resistor R84 within line 558.

Control over frequency and volume thus provided permits a broad flexibility in developing an audibly perceptive cueing to the surgeon using the probe device 12. In particular, it is this control over loudness and frequency which permits the "siren" type output which increases in frequency and volume as the situs of tumor containing more concentrated radiolabel is approached.

Figure 10A:
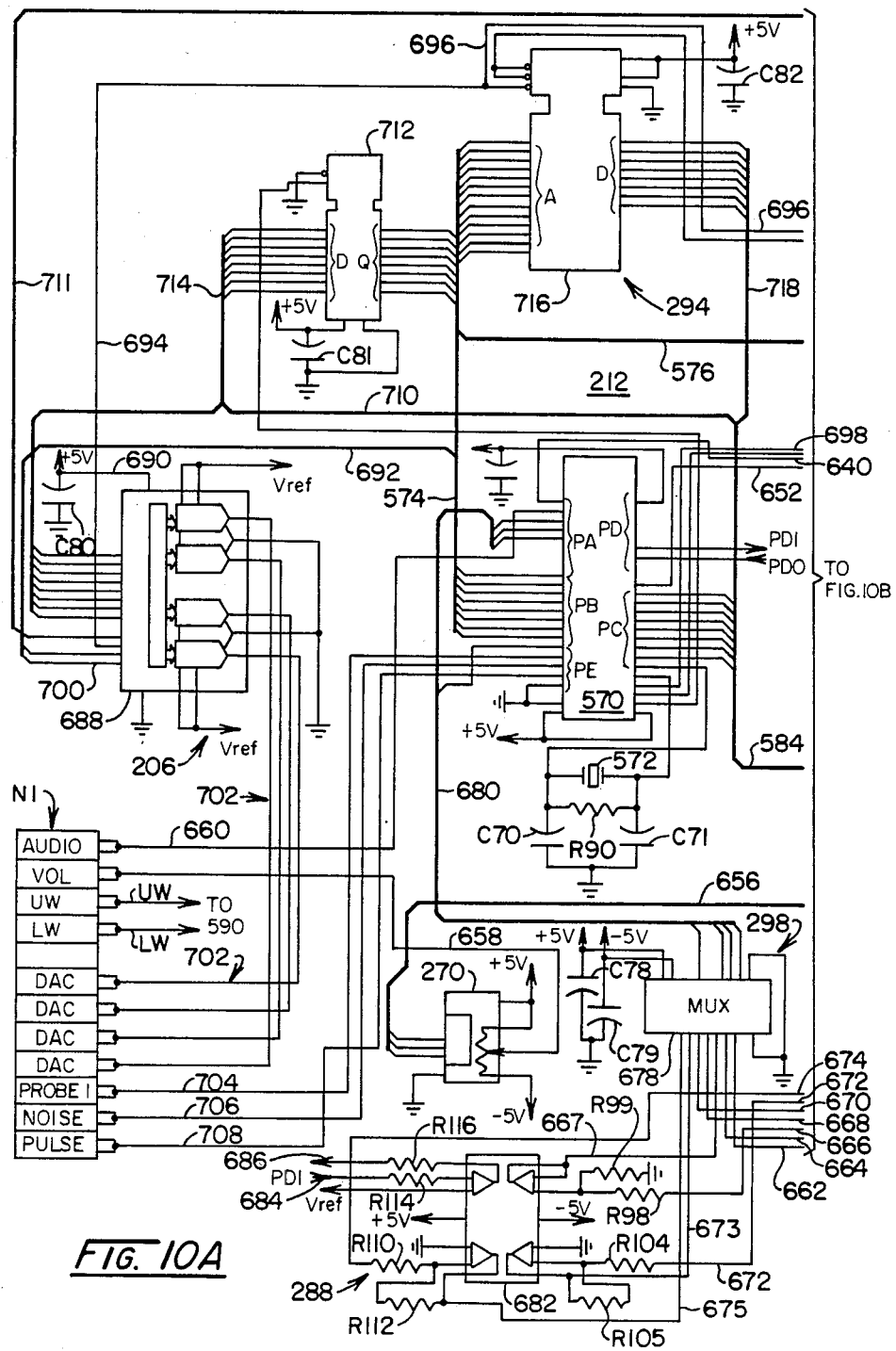
FIGS. 10A and 10B combine as labeled to provide an electrical schematic diagram of the digital components of the apparatus of the invention.
Figure 10B:
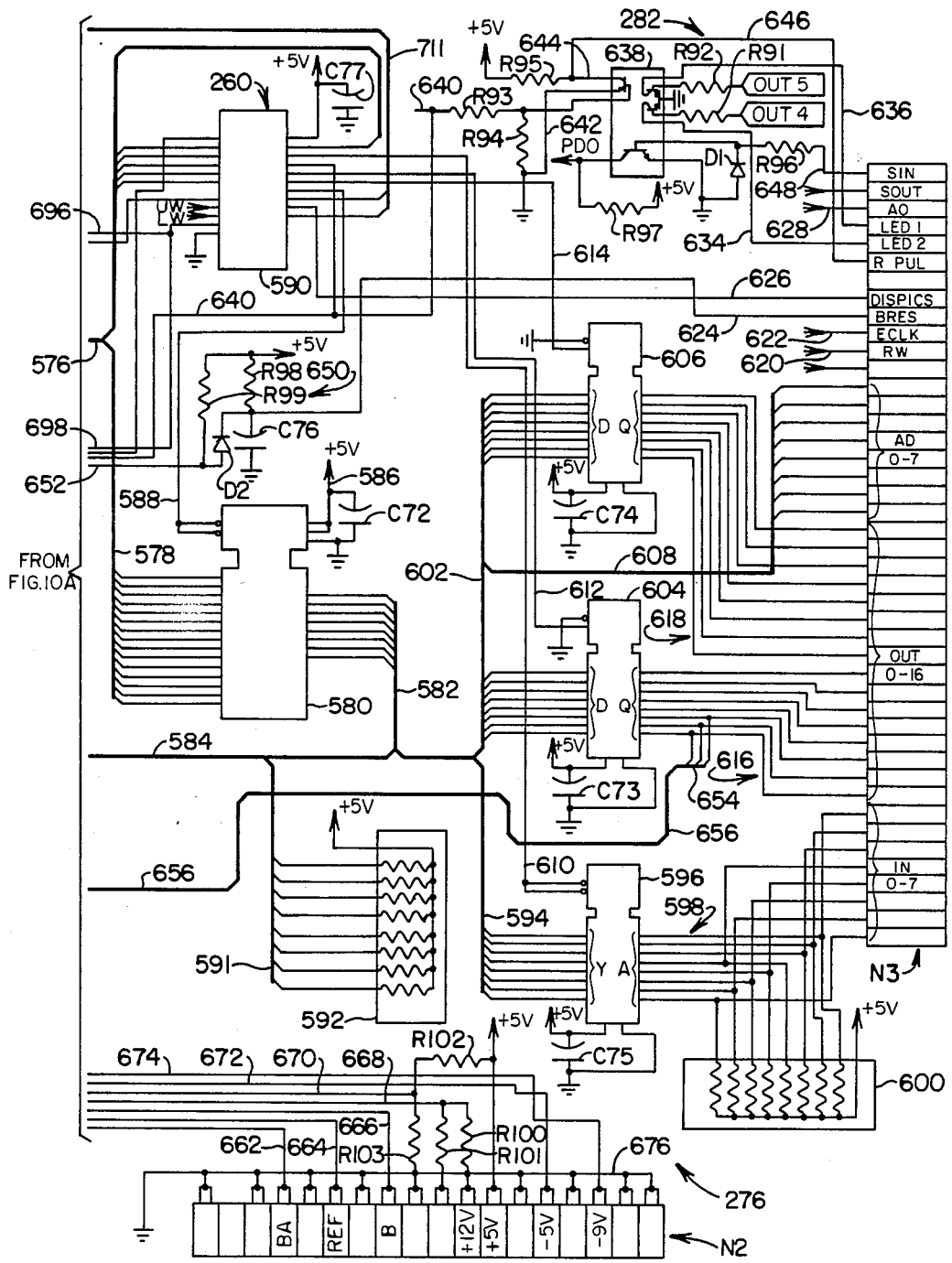

Referring to FIGS. 10A and 10B, the digital or microcomputer driven functions of the control features of the invention are represented at an enhanced level of detail. Looking to FIG. 10A, the principal logic control for the instrumentation seen to be provided by a microcomputer 570 which may be provided, for example as type MC68HC11A8 as marketed by Motorola, Inc. This single-chip microcomputer employs HCMOS technology and includes on chip memory systems including an 8K byte ROM, 512 bytes of electrically erasable programmable ROM (EEPROM), and 256 bytes of static RAM. The device also provides on chip peripheral functions including an eight channel analog-to-digital (A/D) converter, a serial communications interface (SCI) subsystem and a serial peripheral interface (SPI) subsystem. Another feature of the device employed with the instant instrumentation is a pulse accumulator which can be used to count external events (gamma ray related pulses) in an event counting mode. Port groupings on the device are shown labeled as "PA, PB, PC, PD, PE". Clock input for the microcomputer is provided from a four MHz crystal 572 performing in conjunction with capacitors C70 and C71 a well as resistor R90. Device 570 interfaces through an address bus coupled to its PB port at 574 and branching as shown at 576 and 578 with an erasable programmable read only memory (EPROM) 580 having 32K bytes of memory. The corresponding data ports of the device 580 are coupled to data bus 582 shown branching as at 584 to extend to the PC terminals of microcomputer 570 (FIG. 10A). Memory 580 is shown coupled to +5 v at line 586 as filtered by capacitor C72 and is enabled from along line 588 extending to a terminal of an erasable programmable logic device (EPLD) 590 described in conjunction with FIG. 7B at block 260 as a real time pulse discriminator, that numeration also being provided in the instant drawing. Device 590, a type EP600 marketed by Altera Corp. incorporates a large compilation of 600 logic gates which are programmable to develop desired Boolean functions within a single component. It is shown coupled to +5 v supply as followed by capacitor C77.

Data bus branch 584 is seen branching as at 591 for connection with an array of pull-up resistors 592 coupled, in turn, to +5 v.

Branch 584 further extends via branch 594 to the Y outputs of a type 74541 input buffer 596. This device is shown coupled to +5 v supply as filtered by capacitor C75. The lead array extending from the A ports of the device at 598 is coupled to pull-up resistors from the array thereof at 600, whereupon the devices are coupled to ports 0-7 of a connector N3 leading to the keyboard type switches 32-40 at console 16. data bus branch 584 also extends via branch 602 to the D input terminals of type 74574 output latches 604 and 606 shown coupled to +5 v as respectively filtered by capacitor C73 and C74. These latches provide general purpose outputting at 16 locations as labelled at connector N3. via respective lead groupings 616 and 618.

A supplementary branch 608 of the data bus extending from branch 602 is employed for driving the LCD display 26, the outputs being represented as AD0-7 in connector N3. Similarly, read/write information to the display is provided to the connector from line 620; the display clock is driven from line 622; the display reset is provided from line 624; the display select signal is provided from line 626 from device 590; and the I/O port selection of the display is made by signal from line 628, all of the above leading to connector N3 as labeled. Devices 596, 604 and 606 are enabled, respectively, from lines 610, 612 and 614 extending from logic device 590. Drives to the dual LED at 28 of the console 16 as described in FIG. 1 are provided at connector N3 through lines 634 and 636. The latter lines lead to the differential transistor pair of a transistor array component represented at 638. These transistors are selectively actuated from the output ports 4 and 5 of lead array grouping 616 through respective resistors R91 and R92. The transistors of component 638 also may be employed to buffer raw pulse data representing the output of device 590 at line 640 (FIG. 10B). Such an input may be provided from the device 590 at line 640 for assertion through resistor R93 to the base of a buffer transistor within component 638. The emitter of that transistor is coupled via line 642 to ground and resistor R94 to line 640 and the output thereof at line 644 is coupled to +v through resistor R95. A line 646 carries the raw pulse signals to connector N3 for providing availability to them through the back panel of console 16. In similar fashion, the apparatus is capable of receiving serial data in for inputs from a remote facility at connector N3 as attached to line 648. Such information is fed through resistor R96 and directed to the base of a level shifting transistor within component 638 for presentation to the microcomputer input line PD0. The latter line is shown coupled at 5 v through resistor R97. The emitter of the subject transistor within component 638 is coupled to ground and a diode D1 is coupled from the emitter to line 648 for protecting the transistor.

Microcomputer 570 additionally receives a reset from the circuit represented generally at 650 and comprised of capacitor C76, diode D2, resistors R98 and R99. The reset function extends via earlier-described line 624 to connector N3 for purposes of resetting the display 26. Output from the network 650 is through line 652 extending to the reset terminal of microcomputer 570.

Three of the leads of bus array 616 are tapped at line array 654 and directed as represented by bus 656 to the input of an EEPOT described earlier at block 270 in connection with FIG. 7B and shown with like numeration in FIG. 10A. Coupled between +5v and −5v, the device 270 provides a solid-state election of impedance values with memory under the control of the microcomputer 570 from input 656. The resultant output, which may vary between −5v and +5v, is directed along line 658 for outputting at connector N1 leading to line 268 as described in conjunction with FIGS. 9 and 7B. Similarly, the audio squarewave input to line 264 of that volume control function is provided from one PE port of microcomputer 570 via line 660.

Microcomputer 570 is programmed to monitor the power supplies as described at block 180 in FIG. 7B, employing a multiplexing approach as represented by block 298 in that figure. Connector N2 is shown in FIG. 10B carrying the inputs from the various aspects of the power supply. These power inputs are both used by the instant circuitry and monitored by the microcomputer 570 through the noted multiplexer function 298. In this regard, it may be observed that line 662 functions to monitor battery status, while line 664 monitors a voltage reference. These lines are directed to two of the inputs of the multiplexer shown at 678 in FIG. 10A. The bias supply for the crystal 58 of the instrument is monitored from line 666 following a level shifting procedure which, looking to FIG. 10A is provided from one stage of a quad operational amplifier component shown at 682. Note that line 666 extends through resistor R98 into this stage, the latter resitor being coupled with a divider resistor R99 and the output of the level shifting stage being provided at line 667 which extends to another input of the multiplexer 678. In similar fashion the +12 v power supply is coupled through resistor R110 by line 668 and is additionally coupled to ground through resistor R101 and line 676. Line 668 is seen directed to another input of multiplexer stage 678. The +5 v supply is adjusted by resistors 102 and 103 and submitted via line 670 to a multiplexer stage 678. The −5 v supply is monitored from line 672 which is seen to extend through resistor R104 to another level shifting stage of component 682. The shifting further is affected by feedback resistor R105 and the resultant output to multiplexer stage 678 is provided at line 673. Finally, the −9 v supply introduced at connector N2 is monitored by line 674 which extends through resistor R110 to another level shifting stage of component 682, the level shifting further being controlled from feedback resistor R112 to provide an output to the multiplexer stage 678 from line 675. Note that line 676 couples intermediate components of connector N2 to ground.

FIG. 10A further reveals that the fourth amplifier stage of component 682 is used to provide a serial output port, the stage receiving the noted reference signal as provided at connector N2 and being presented with pulse data as an input through resistor R114 at line 684. The level shifted signal then is asserted at line 686 through resistor R116.

FIG. 10A also reveals the presence of a quad digital-to-analog converter component described earlier in conjunction with block 206 in FIG. 7A and represented in general by the same numeral. The component, shown at 688 is coupled to +5 v at line 690 as filtered by capacitor C80 and is controlled from microcomputer 570 via address bus 584 and branch 710 as well as bus 692 and lead grouping 700. Read/write commands are asserted from the microcomputer 570 through a circuitous arrangement including lines 694, 696 and 698, while the chip select input thereto is provided from 711 extending from device 590 (FIG. 10B). The four channels of output from device 688 are shown at line grouping 702 leading to corresponding connectors within the connector component N1. These devices extend, for example, to the two squarer networks described at blocks 248 and 250 in FIG. 7A as well as the rate amplification network 312 described in that figure and the normalizing amplifier described at block 204 in that figure. Also shown entering the connector N1 are the upper window pulses and lower window pulses respectively developed at lines 256 and 258 (FIG. 8B) which are directed as labeled, to the corresponding inputs at component 590 (FIG. 10B). Additionally, the probe current monitored output at line 352 (FIG. 8A) enters for assertion at a PE terminal of microcomputer 570 via line 704. Further, the output of the noise averager networks shown at block 218 in FIG. 7A and developed at line 220 are presented to connector N1 and conveyed to microcomputer 570 via line 706. The corresponding pulse acquisition output, as described in conjunction with block 224 in FIG. 7A, is shown entering through connector N1 for presentation to the microcomputer 570 via line 708. Address bus 574 is seen to extend to the Q input terminals of an address latch 712. Provided as a type 74573, the latch functions as a portion of a memory interface saving lower data bits and converting them to addresses. The output of the latch 712 as coupled to the branch 714 of data bus 710. Latch 712 is coupled to +5v as shown which is filtered by capacitor C81.

Address bus 574 also is seen being directed to the A terminal input of a real time clock and calendar component described in conjunction with block 294 in FIG. 7B and shown with the same numeration herein. Marketed as a type DS1216 component by Dallas Semi-Conductor, Inc. the device incorporates an embedded lithium energy cell such that CMOS static RAMs associated therewith can be converted to non-volatile memory. The device keeps track of hundreds of seconds, seconds, minutes, hours, days, date of the month, months and years. These data may be of considerable value in maintaining research statistics in conjunction with the instrumentation 10. The device as represented at 716 is coupled to +5v as filtered by capacitor C82 and the D terminals thereof are coupled to data bus via branch 718.

As indicated earlier herein, for surgical utilization, it is necessary that the instrument 12 be maintained in a clean and sterile condition prior to its implementation within the surgical theater. Thus, the outer surface of the device is polished for ease in cleaning contaminants therefrom and the assemblage is suitable for sterilization preferably by gaseous treatment.

A technique which both simplifies cleaning the instrument and maintaining its sterile condition involves the use of a disposable plastic cover which fits over the probe device 12 and which is formed of a polymeric material which is readily produced in a sterile state. Thus, prior to an operation, the surgical personnel will slide the probe within the cover or sheath. The addition of the polymeric surface aids in the control of vibration induced noise as well as representing an ideal technique for maintaining the requisite sterile condition for the device. Looking to FIG. 11, the instrument 12 is shown in dashed line fashion within a polymeric cover 730. The cover 730 includes a nose portion 732 formed of a tough plastic having a thickness, for example, of 0.020 inch. This will protect the cover 730 from tearing or the like when used in the rigorous activities of surgery. From the nose portion 732 the sheath may extend rearwardly a sufficient length to cover the signal transmission components as at 14 for a sufficient distance to assure sterile integrity.

Periodic calibration is an important aspect of operating the apparatus 10. In this regard, a check source is employed preferably which is readily positionable over the forward portion 20 of the probe instrument 12. Additionally, a noise adjustment fixture is employed which is structured to temporarily shield the detector components from local sources of radioactivity, i.e. within the surgical theater. Turning to FIGS. 12 and 13, such a noise adjustment fixture is represented generally at 734. Looking to FIG. 13, the component 734 is seen to be formed having an outer cup-like portion 736 formed of a radiation attenuating material such as lead having a thickness, for example, of 0.125 inch. Within the outer cup 736 is a center cup 738 fashioned of a smooth, soft washable material such as teflon, nylon or the like. A loose fit over the portion 20 of the instrument 12 is desired. This arrangement functions to block such local sources. A check source retainer is formed in similar fashion as the inner cup 738 to fit over forward portion 20 of the instrument. Again using cup 738 as exemplary of this check source feature, within the center portion 740 (FIG. 13) of the cup 734 there would be positioned a check source of radiation of relatively low energy but extensive half life. For example, Iodine 129 represents a viable material for this purpose.

The general program under which the microcomputer 570 performs is represented in flow chart format in FIG. 14. Referring to the latter figure, the start of the main program is represented at node 750 which is shown directed via line 752 to the self-diagnostic and initialization procedures represented at block 754. Following such initialization, as represented at line 756, the main program proceeds to display screen information to the operator as represented at block 758. The particular information displayed is determined with respect to the particular type of utilization being made of the instrument 12. In general, however, the main program reacts to an interrupt generated from the "keyboard" represented by the switches on the console 16 represented in general at 30. Accordingly, the program progresses as represented at line 760 to the inquiry at block 762 determining whether or not a keyboard switch has been depressed. The keyboard 30 is sampled on about 10 millisecond intervals for a valid character, i.e. one which passes a simple "debounce" test. In the event there is no valid keyboard switch depression, then as represented by loop line 764, the main program returns to line 760 to again await the depression of a switch by the operator. In the event a valid key or switch depression has been detected, then as represented at line 766, the main program performs in accordance with the function of the key so depressed. This will include the depression of up-down arrow switches as at 39 and 40, alteration of mode count technique 34, and the like. Following the carrying out of the function associated with the noted switch, as represented by line 770, the program returns to line 756 again to display screen information corresponding with the keyed instruction and again to await a key interrupt.

Looking to FIG. 15, the main or general interrupt routine of the program is revealed as starting at node 772. As represented at line 774, the interrupt routine initially saves register information, as represented at block 776. Then, as represented at line 778 and block 780, an inquiry is made as to whether the key information received is valid. For example, for a valid switch depression to be recognized, at least two interrupts are required. In the event that a valid key or switch depression is detected, then as represented at line 782 and block 784 a filtering function is carried out to determine whether or not the off switch 33 has been depressed. In that event, then there is no rationale for continuing with the active program. Thus, assuming that the off button has been depressed, as represented at line 786 and block 788 a check sum is prepared to assure that the data in memory are valid and the information is then saved in non-volatile memory (EEPROM), it being recalled that the microcomputer 57 has 512 bytes of such non-volatile memory. The program then proceeds, as represented at line 790 and at block 792 to turn off the system, whereupon as represented at line 794 and node 796, the interrupt routine is ended.

Figure 16:
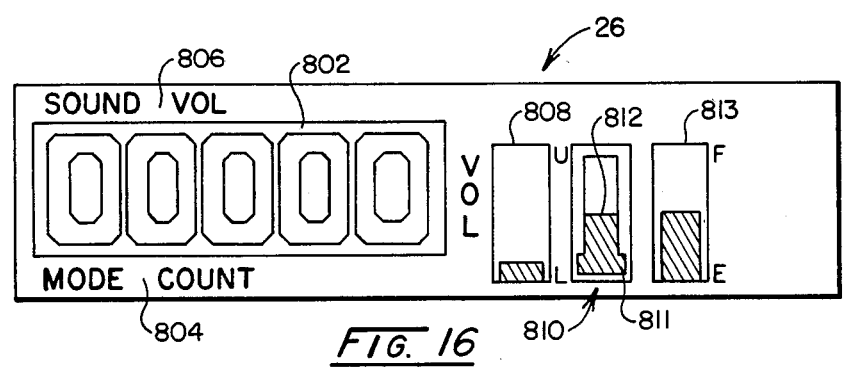
FIG. 16 is a schematic representation of a readout provided with the console shown in FIG. 1.

Assuming that the off button was not actuated, then as represented at line 798 and block 800, the interrupt routine determines whether the reset count switch 36 of console 16 has been depressed. Generally, the pulse counting procedure is one having several modes of operation. In its most simple performance, an event count which is identified at display 26 as "mode count" provides a straight-forward accumulation of counts in incrementation of the display. Looking momentarily to FIG. 16, the display is revealed for this orientation. The LDC output of large numbers at 802 provides the numeric readout of the accumulated counts. Actuating the reset count button or switch 36 resets this published count to zero on the fly, is it were. This particular mode is sometimes used for checking or adjusting the instrument. The mode count identification in the display is published as reverse video readout at region 804. Note additionally on the display that a "SOUND VOL" readout is supplied above the numerals at 806 which, when active, will be represented in reverse video. The particular audio volume is selected by the operator by pushing switch 35 and manipulating up-down buttons switches and 40 in conjunction therewith. The display 26 provides a bar graph representation of selected volume as shown at 808. Display 26 also will portray upper (U) and lower (L) comparator window settings as a chart shown at 810. The lower portion of this chart at 811 shows noise level, the above which pulse height is portrayed at 812. Window limits (U,L) are represented by labelled horizontal dashes. Additionally, display 26 will show battery charge status in bar chart form as at 813.

The count modes which are selected by actuating switch 34 in conjunction with up-down switches 39 and 40 includes a time count which is a straight-forward accumulation of counts for a specified interval. A next count in this mode is initiated by depressing reset count 36. Counting intervals of, 1, 2, 5, 10, 20, 30, 50, 60 and 100 seconds are selectable in the count mode using switches 39 and 40. A rate mode also is selectable within the count mode election at switch 34. For that mode arrangement, the display at 804 will read "MODE RATE CPS". Correspondingly, where the noted timed modes are available, the display at region 804 will read "MODE COUNT/SEC" (see FIG. 22). Two seconds is a default value for this feature in the event the operator has picked no others. The count mode switch 39 actuation also provides a time to preset function which is a useful constant accuracy mode of operation. In this mode, preset counts of 100, 200, 500, 1,000, 2,000, 5,000 and 10,000 are selectable, 100 counts being a default value. The counter and readout 802 increments from zero to the selected preset value and holds. Thus, the display shows the number of gamma rays counted until it reaches that preset number, whereupon it switches to show the number of seconds required to reach the preset count. The reset key 36 resets the display to zero and initiates any next counting sequence. Accordingly, the count mode switch 34 initiates this count mode and the up/down arrow switches 39 and 40 may be actuated by the operator to develop "COUNT", "TIME COUNT", "RATE", "TIME TO PRESET" and "OFF" displays and modes of performance.

Returning to FIG. 15, in the event the reset switch 36 has been actuated, then as represented at line 822 and block 824, the data count is reset to zero, the LED 28 is illuminated green and the collect mode recommences as the program continues as represented at line 826.

In the event that no reset actuation has been observed, then as represented at line 828 and block 830, switch information is saved and the program continues as represented at line 832 to the inquiry at block 834 to determine whether it is appropriate to update the display 26 and real time clock information. Also associated with line 832 is the path line 836 from block 780 showing that the program defaults to this position in the event no valid switch actuation has been detected. In the event the appropriate timing is at hand to update the real time information, then as represented at line 838 and block 840 a substantial amount of updating occurs.

A desirable aspect of the operation of the instant instrumentation resides in its capability for accumulating pulses such that the microcomputer 570 is not called upon to sample periodically to look for received count. As a consequence, no "dead time" between sampling is present within which any counts might be lost. An 8-bit register within the device 570 permits a gathering of up to 255 events or counts before it must be read or overflows. Thus, the register may be read at a 10 millisecond interrupt rate without resort to time critical subroutines attempting highly rapid polling procedures. As shown in block 840, the updating includes the display 26 data, sound information in terms of volume and the like, the real time clock, the time spent counting and all counting modes and information. Following such update, as represented at line 842, the routine returns to line 844 also representing a determination that the time for updating has not occurred as developed at the inquiry at block 834. The program then turns to the instructions at block 846 where the registers are stored and the interrupt routine is terminated as represented by line 848 and end node 850.

As part of the interrupt updating, the program also evolves count rate information which has particular utilization in the surgical guiding feature of the instrumentation of the invention. Looking to FIG. 17, this interrupt update routine is revealed as commencing at block 852, the program commencing as represented by line 854 and block 856 to read the count register. As represented at line 858 and inquiry block 860, a determination is made as to whether a one second collection interval has elapsed. If such is the case, then as represented at line 862 and block 864, the count total then is made equal to the previous counts and the counts in the register. As represented then at line 866 and block 868, the rate is computed as the total counts divided by time which may be either a one second interval or a 60 second interval. The program then progresses as represented at line 870 and block 872 to display the updated information as to rate.

In the event the determination at block 860 is in the negative, then as represented at line 874 and block 876, an inquiry is made as to whether 1/10 second has elapsed. If 1/10 second has not elapsed then, as represented at line 878 and block 880, no number of counts is saved and the register is updated. As represented at line 882 and node 884, this portion of the update routine then is concluded. On the other hand, should the inquiry at block 876 determin that 1/10 second has elapsed, then as represented at line 886 and block 888, the previous number of counts is added with the new information from the count register and, the routine continues as represented at line 890 and block 820, the rate is computed with respect to the 1/10 second interval. The program then progresses to earlier described block 872 as represented by line 894. Upon completion of display update, then as represented at line 896 and block 898, the rate information as developed by the 0.1 second incrementation is saved for purposes of updating the siren audio output of the system which is used in immunoguided surgery. As represented at line 900 and node 902, the routine then is completed.

Figure 18:
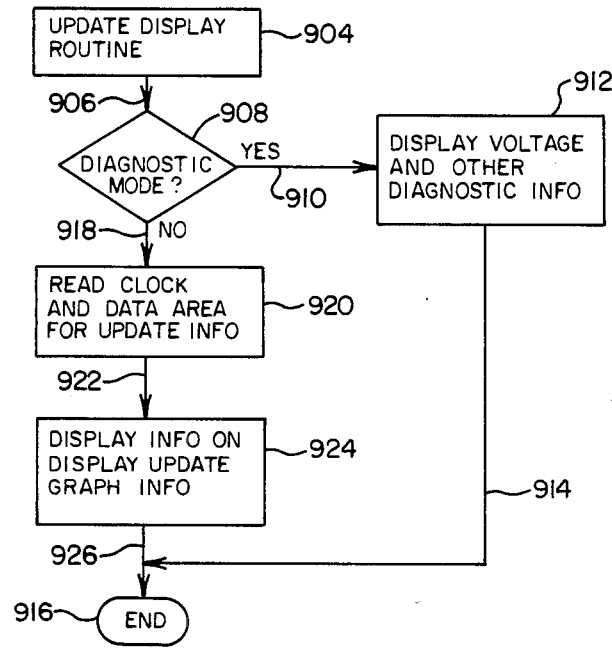
FIG. 18 is a flow chart showing the display update routine employed with the control features of the apparatus of the invention.

Turning to FIG. 18, another portion of the update display routine described in connection with FIG. 15 is represented, the latter display updating function being represented at block 904. This routine progresses as represented at line 906 and block 908 to a determination as to whether the diagnostic mode has been called for. This mode is accessed by a combination of switch actuations at array 30 and is used mostly by maintenance and factory personnel, for example, to establish selected bias for the crystal 58. The mode derives readouts for various voltage levels which can be adjusted in conjunction with observing the readout. Thus, if the diagnostic mode is detected, then as represented at line 910 and block 912, the voltage and other diagnostic information is displayed. The routine then exits as represented at line 914 and node 916.

Where the diagnostic mode is not present, as represented at line 918 and block 920, the program then reads the real time clock and updates the main display information. The program then proceeds as represented at line 922 and block 924 to display the information so updated and further updates graph displays, for example, such as that shown in FIG. 16 at 808, 810 and 813 showing audio volume level for the readout, pulse and noise levels and battery condition. The routine then proceeds to end as represented by line 926 leading to node 916.

Figure 19:
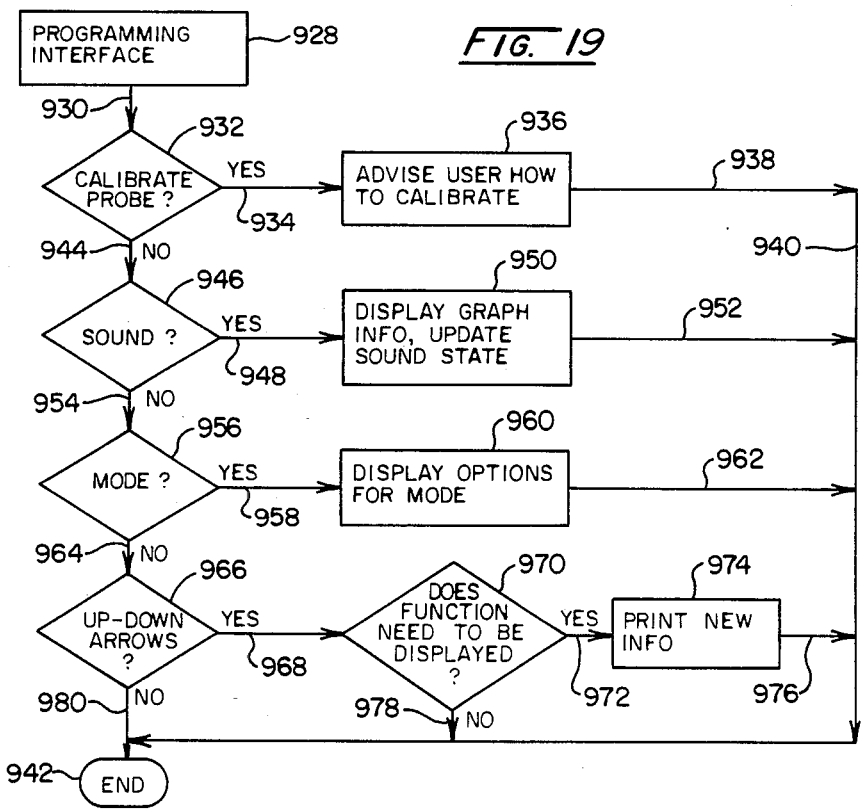
FIG. 19 is a flow chart showing the programming interface features of the control components of the apparatus of the invention.

Turning to FIG. 19, the programming interface routine which essentially is part of the routine of FIG. 14 is represented as commencing at block 928 and line 130 to the determination as to whether a calibration as called for by switch 38 of console 16 has been called for. In the event that it has, as represented at line 934 and block 936, the display 26 commences to read out instructions in a user friendly manner for the attachment of the noise adjustment fixture as described at 734 in FIGS. 12 and 13 and subsequent adjustment of the device. Following such adjustment and completion of the instructions displayed, then as represented at lines 938, 940, and 942, the programming interface mode ends. If the calibration mode has not been called for, then as represented by line 944 and block 946 the program then inquires as to whether the sound mode has been called for by actuation of switch 35. If that is the case, then as represented at line 948 and block 950, the display 26 shows graphic information as to volume level as shown at 808 in FIG. 16 and updates the particular sound state called for. In particular, the up/down switches 39 and 40 may be employed to elect a "click" type sound reminiscent of a Geiger counter, a "beep" sound of longer duration, the earlier-noted siren tone, the frequency of which varies with the radiation level detected. This tone enables the user to detect evidence of variations in radioactivity levels while watching the position of the probe itself. Finally, an OFF election may be made in this mode. Following the updating of information elected by the user, then as represented at line 952, the routine exits as represented by lines 940 and node 942.

In the event the determination at block 946 is that the sound mode was not entered, then as represented by line 954 and block 956 a determination as to what mode for counting has been elected. This mode is entered by the actuation of switch 34 upon console 16. In the event the mode is elected, then as shown at line 958 and block 960, the various options for this mode are displayed at display 26. The options will include the earlier-discussed "TIME COUNT", "RATE", and "TIME TO PRESET" which, in turn, lead to additional dialogues with the user. As before, the up/down switches 39 and 40 adjust rates within the count mode election; they adjust volume; and they carry out calibration adjustments. In effect, these switches provide a change of value or adjustment within a current function within which the system is operating. Following the adjustment and display as represented at block 960, as shown at lines 962 and 940 and mode 942 this routine ends.

In the event the determination at block 956 is in the negative, then as represented at line 964 and block 966, the system then considers the above-described actuations of switches 39 and 40 with the up/down functions. Where those switches have been actuated, then as represented at line 968 and block 970, a determination is made as to whether by so actuating either of these switches, the resultant election should be displayed such as the counts per second or counts per minute rate and the like. Where such display should be made then, as shown at line 972 and block 974 the new information is displayed and as represented at line 976 and line 940, the routine exits as repesented at node 942. Where no new function may be displayed, as determined at 970, then as shown at line 978 and line 940, the routine exits as represented at line 942. Similarly, where these switches 39 or 40 have not been actuated, then as represented at line 980 leading to node 942, the routine ends.

Figure 20:
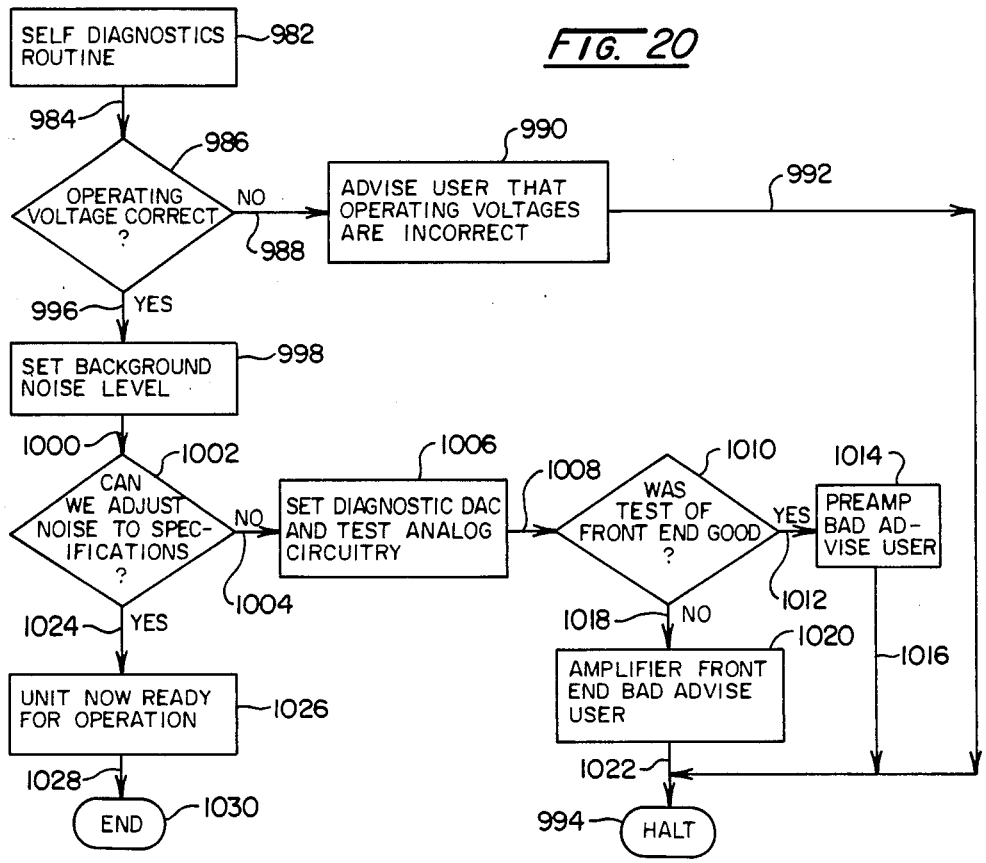
FIG. 20 is a flow chart showing the self-diagnostic routine carried out by the control features of the invention.

Turning to FIG. 20, a self-diagnostic routine is represented as commencing at block 982. This self-diagnostic routine may be used a number of times during the main program, its most important application being at the commencement of any given use. The program commences as represented at line 984 to the inquiry at block 986 wherein a determination of the appropriateness of the operating voltages is made. This activity includes the monitoring evaluations made in conjunction with connector N2 as described in conjunction with FIG. 10B, and includes an update on battery charge status. In the event that these conditions so monitored are incorrect, then as represented at line 988 and block 990, the user is advised at display 26 that the operating voltages are incorrect, and as represented at line 992, the program is brought to a hault as represented at node 994. Where all monitored parameters are correct and the probe 12 is appropriately mounted or attached to console 16 then as represented at line 996 and block 998, the background is evalutated and this background will include cosmic disturbance, normal electrical noise and the like. Recall that this adjustment is made from the digital-to-analog converter function described at block 206 in FIG. 7A. Following setting of this background noise level, as shown at line 1000 and block 1002, a determination is made as to whether adjustment can be made within specification. In the event that the noise adjustment is without specification values, then as represented at line 1004 and block 1006, the diagnostic digital-to-analog converter input is set as described at line 314 in FIG. 9, the self-test pulsing at line 322 is carried out and, the "front end" analog circuit including FIGS. 8A-8C is tested with a diagnostic pulse. Then, as represented at line 1008 in block 1010, a determination as to whether analog circuitry (front end) was performing correctly with the test pulse is made. Where that is correct, then as represented at line 1012 and block 1014, a determination is made that the preamplification stage within the instrument 12 is defective and the user is so advised at display 26. As represented at lines 1016 and 992, leading to node 994, the program then halts. Where the indication of the front end test at block 1010 shows that the analog circuitry was not functioning properly, then as represented at line 1018 and block 1020, the user is advised at display 26 that the analog circuitry or "front end" is defective. The routine then proceeds as represented at line 1022 to halt as indicated at node 994.

Where the indication that the noise is adjustable to specification is made, then the program proceeds as represented at line 1024 and block 1026, the unit is ready for operation and as represented at line 1028 and node 1030, the routine ends.

Figure 22:
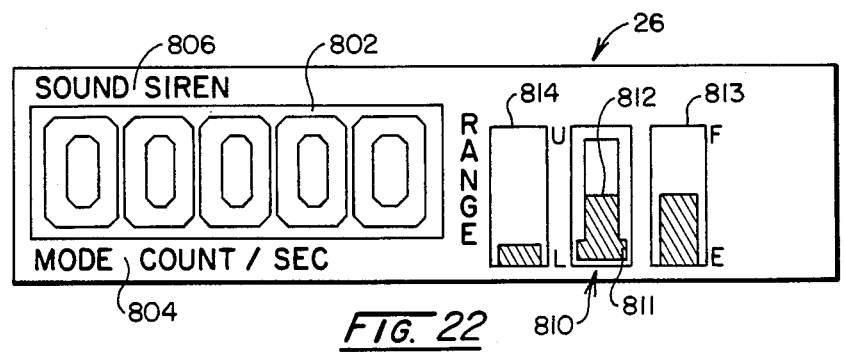
FIG. 22 is a schematic representation of a display which may occur at the readout of the console shown in FIG. 1.
Figure 21:
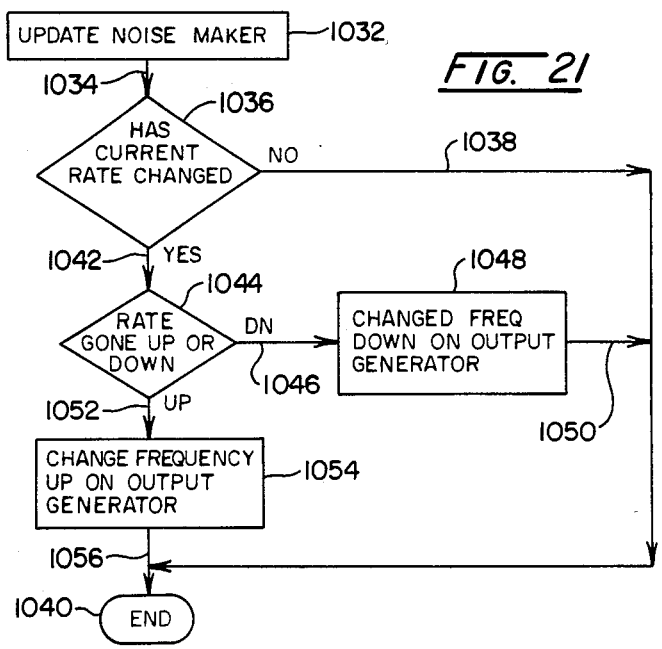
FIG. 21 is a flow chart showing the technique for carrying out siren type audio outputs employed as part of the control features of the apparatus of the invention.

As described in conjunction with the flow chart of FIG. 17, the microcomputer 570 continuously updates the value of the count rate. This feature is used to update the status of the sound output function of the instrument. Looking to FIG. 21, the routine under which the siren perceptive output is achieved for immuno-guided surgery is portrayed as "Update Noise Maker" represented at block 1032. This routine commences at line 1034 to the inquiry at block 1036 wherein a determination is made as to whether the current pulse rate has changed. Where that is not the case, then no alteration takes place in the sound output parameters and the routine exits a represented at line 1038 and end node 1040. However, where the current rate has changed as determined at block 1036, then as represented at line 1042 and block 1044 an increasing (up) or decreasing (dn) rate condition is evaluated. If the rate has gone down, then as represented at line 1046 and block 1048, the frequency applied at line 264 (FIG. 9) is diminished and, as represented at lines 1050 and 1038, the routine ends as represented at node 1040. However, where the rate has gone up, then as represented at line 1052 and block 1054, the frequency is altered to rise and, as represented at line 1056 and node 1040, the routine exits. With this routine, the so-called siren tone may move from a "growl" on and off sound essentially near background radiation levels to a siren tone as the target area is encountered, the sound witnessed usually represents a dramatic increase in pitch as increasing radiation levels are encountered. As shown in FIG. 22, the siren indication is provided at region 806 of display 26, while the range mode is displayed at readout 804 in conjunction with the range graphics at region 814. When the range switch 37 is actuated, or held down, the siren tone will be elected, a bar graph 814 displaying threshold of the siren tone being shown. The range functon adjustment permits adjustment of the device by switches 39 and 40 so as to be silent for background levels but to commence siren audibles when a more radioactive area is scanned. In practice, the range function is often adjusted with the up/down switches 39 and 40 in conjunction with this siren operation.

Figure 23:
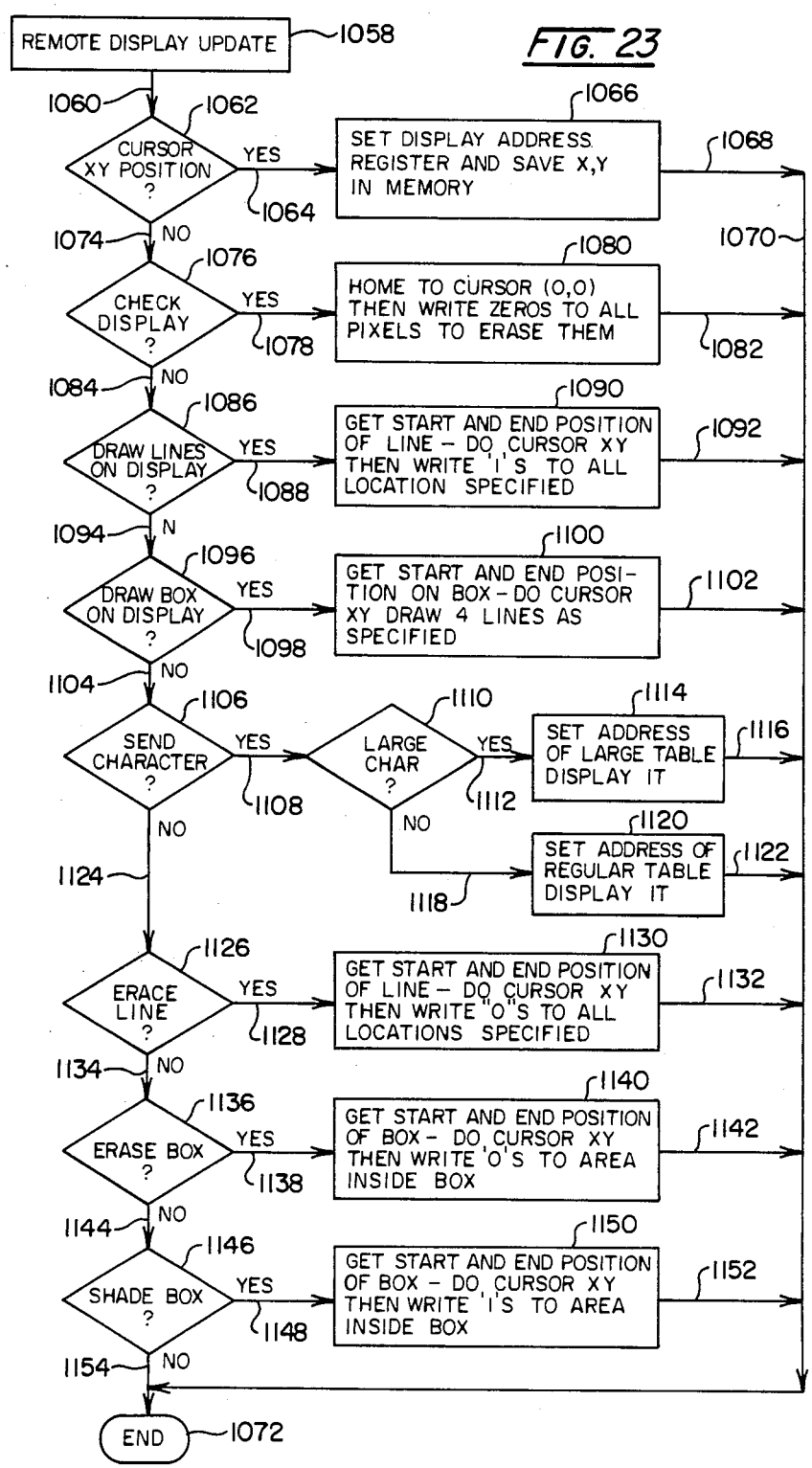
FIG. 23 is a flow chart showing the remote display update routine employed by the control features of the apparatus of the invention.

Turning to FIG. 23, a remote display update routine is shown commencing at block 1058 and the routine is designed with respect to the Hitachi type LM213B dislay device 26 which is operated in a graphics mode both for characters and graphics. The routine commences at line 1060 wherein the x,y position of the display cursor is located. Where such location is determined, then as represented at line 1064 and block 1066, the display address register is set and the x,y coordinates of the cursor are retained in memory. The routine then exits as represented at line 1068 and node 1072. However, where an ongoing cursor activity is not present as represented at line 1074 and block 1076, a determination is made as to whether the display has been cleared. If that is the case, then as represented at line 1078 and block 1080, the cursor is homed to its initial 0,0 position and zeroes are written to all pixels to erase the display 26. As represented at lines 1082, 1068 and node 1072, the routine then ends. Where the display is not cleared, then as represented at line 1084 and block 1086, a determination is made as to whether it is necessary to draw lines on the display. If that is the case, then as represented at line 1088 and block 1090, the starting and end positions of any given line are located and the cursor x,y coordinate orientations are such as to fill in the lines between those two end locations in horizontal and vertical orientations. The routine then exits via lines 1092, 1068 and node 1072.

Where the draw lines routine is not called for, then as represented at line 1094 and block 1096, an inquiry is made as to whether a box or rectangular drawing is requested. In the event that is the case, then as represented at line 1098 and box 1100, the start and end positions of the rectangular structure are located and four lines defining the rectangular form are filled in. The routine then exits as represented by lines 1102, 1068 and node 1072. Where the box drawing is not called for, then as represented at line 1104 and block 1106, an inquiry is made as to whether a character is to be displayed. If that is the case, then as represented at line 1108 and block 1110, a determination is made as to whether a large or small character is to be displayed, such variation character size being observable from FIGS. 16 and 22. Where a large character is appropriate, then as represented at line 112 and block 114, a memory accessed appropriate address for the elected character of large format and the character is displayed. The routine then exits as represented at lines 1116 and 1068 to node 1072. Where a large character is not elected as at block 110, then as represented at line 1118 and block 1120, the regular character table is accessed and such character is displayed of smaller format. The routine then exits as represented at lines 1122, 1068 and node 1072.

Where no characters are to be displayed, then as represented at line 1124 and block 1126, inquiry is made as to whether a line should be erased. In the event that is the case, then as represented at line 1128 and block 1130 the start and end positions of the line in question are accessed and zeroes are written at the specified locations. The routine then exits as represented at lines 1132, 1068 and node 1072.

Where no line is to erased, then as represented at line 1134 and block 1136, the equivalent inquiry is made as to whether a box or rectangle is to erased. Where that is the case, then as represented at line 1138 and block 1140, the starting and end positions for the box or rectangular figure are located and zeroes are written at the starting and end points appropriate to carry out erasure. The routine then ends as represented at lines 1142, 1068 and node 1072.

Where no rectangle erasure is at hand, then as represented at line 1144 and block 1146, a determination is made as to whether any shading is required within a box, i.e. to show a bar graph or the like. In the event that is the case, then as represented at line 1148 and block 1150, start and end positions of the box with respect to this shading are determined and ones are written to form the shading. The routine then ends as represented at lines 1152, 1068 and 1072. As represented further at line 1154, this is the final inquiry in the display update, the latter line leading to end node 1072.

Figure 24:
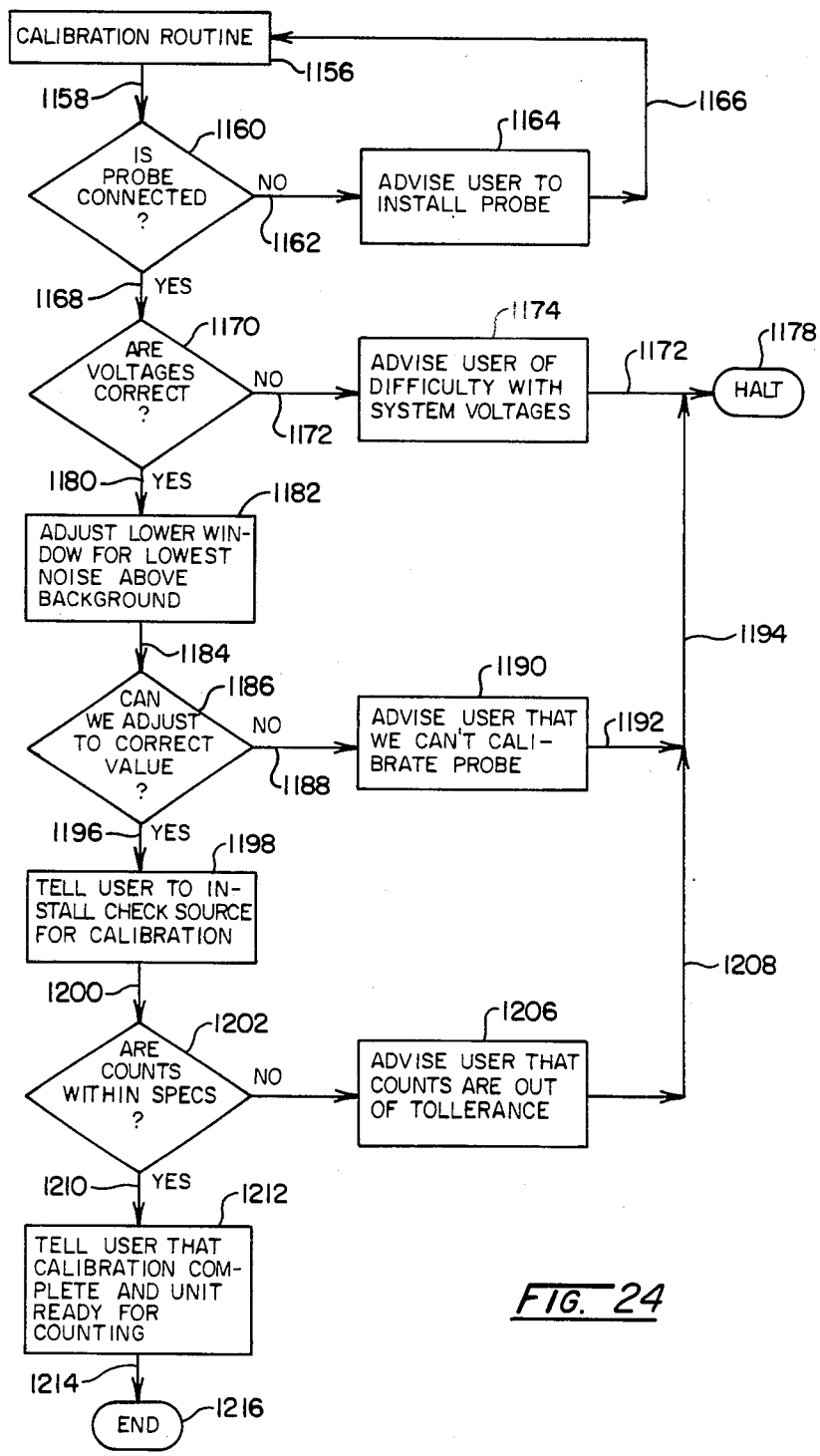
FIG. 24 is a flow chart showing the calibration routine carried out by the control features of the apparatus of the invention.

Turning to FIG. 24, the calibration routine is represented commencing at block 1156 with the actuation by the user of the calibrating switch 38 upon console 16. At the commencement of this routine, as represented at line 1158 and block 1160, a determination is made as to whether the probe instrument 12 is properly connected. This is carried out through the earlier-described measurement of probe current as described in FIG. 7A in conjunction block 188. In the event the probe device 12 is not properly connected, then as represented at line 1162 and block 1164, the display 26 advises the user to install the probe and the routine recommences as represented by loop line 1166.

Where the probe is appropriately connected, then as represented at line 1168 and block 1170, a determination is made as to whether the power supply voltages are correct. As discussed above, this involves the monitoring of the input supply voltages including bias to crystal 58 as described in conjunction with FIG. 10B at connector N2 and FIG. 10A in conjunction with multiplexer 678. If the determination as to voltage levels finds error, then as represented at line 1172 and block 1174, the display 26 advises the user of difficulty with system voltages and, as represented at line 1176 and node 1178, the system halts until correction can be effected.

Where the test for supply voltages shows them to be at valid levels, then as represented at line 1180 and block 1182, the lower window of acceptance is adjusted for the lowest noise level above background, the latter values, for example, being attainable from the noise averager network as described at block 218 in conjuction with FIG. 7A. Following the attempted adjustment, as represented at line 1184 and block 1186, a determination is made as to whether adjustment of the lower window can be made to an appropriate value. In the event that it cannot, then as represented at line 1188 and block 1190, the display 26 is employed to advise the user that the instrument cannot be calibrated and the routine exits as represented lines 1192 and 1194 to node 1178 to halt.

Where lower window settings can appropriately be developed, then as represented at line 1196 and block 1198, the user is instructed via display 26 to install the check source as described above in conjunction with FIGS. 12 and 13. The routine then continues as repesented at line 1200 and block 1202 to determine whether or not the counting carried out with the check source, for example using Iodine 129, is appropriate, this internal counting will take place over an interval, for example, selected as 5 or 10 seconds. Where the counts or pulses detected are without proper tolerances, then as represented at line 1204 and block 1206, the display 26 is employed to advise the user that the counts received are out of tolerance and, as represented at lines 1208 and 1194 leading to node 1178, the system halts. However, where the counts using the check source are within tolerance, then as represented at line 1210 and block 1212, the user is advised through the display 26 that the calibration is complete and the unit is ready for operation. The routine then ends as represented at lines 1214 and node 1216.

Since certain changes may be made in the above-described system and apparatus without departing from the scope of the invention herein involved, it is intended that all matter contained in the description thereof or shown in the accompanying drawings shall be interpreted as illustrative and not in a limiting sense.

We claim:

1. An instrument for detecting and locating sources of radiation emission, comprising:
    a housing having a first portion having sidewalls formed of select gamma radiation attenuating material and exhibiting an electrical shielding effect and extending to a forward opening positionable proximate said source, and a hand graspable second portion extending from said first portion;
    window means for permitting gamma radiation transmission through said forward opening while blocking the passage of light;
    a gamma radiation responsive crystal positioned within said first portion having a forward surface disposed toward said window means and a rearward surface;
    a thin, gamma radiation transmissive and electrically conductive first insert positioned adjacent said crystal forward surface;
    electrically conductive contact means positioned adjacent said crystal rearward surface for effecting application of an electrical bias thereto and conducting gamma ray induced signal charges therefrom and having a rearwardly disposed portion;
    blocking means formed of a gamma radiation attentuating material postioned within said housing first portion and adjacent said contact means rearwardly disposed portion for blocking entry of radiation toward said crystal rearward surface;
    compression means within said housing first portion spaced from said window means a predetermined amount establishing a dead space therebetween, including a compressible foamaceous material and a retainer transparent to said radiation retaining said foamaceous material in compression against said crystal forward surface for effecting a conforming compressive relationship between said crystal forward surface and said first insert and between said crystal rearward surface and said contact means; and
    circuit means within said housing for applying said electrical bias through said contact means, and including amplifier means and for receiving and electrically treating said signal charges to provide output signals.

2. The instrument of claim 1 further including a thin, radiation transmissive and electrically conductive second insert positioned within said housing first portion having one surface adjacent said window means and an oppositely disposed surface confronting said dead air space.

3. The instrument of claim 1 in which said first insert is a sheet of carbon filled silicon rubber.

4. The instrument of claim 1 further including a thin, compliant, adherent electrically conductive second insert intermediate said contact means and said crystal rearward surface.

5. The instrument of claim 4 in which said second insert is a sheet of carbon filled silicon rubber.

6. The instrument of claim 1 including a thin, compliant, adherent electrically conductive third insert positioned within said housing first portion against said window means.

7. The instrument of claim 1 in which:
    said first insert comprises an electrically conductive polymeric sheet having an adherent surface property adjacent said crystal forward surface; and
    further including a second insert comprising an electrically conductive polymeric sheet having adherent surface properties positioned intermediate said contact means and said crystal rearward surface.

8. The instrument of claim 1 in which:
    said blocking means is formed of a slug of said radiation attenuating material slideably insertable within said housing first portion and having a passageway formed therethrough;
    including insulating means intermediate said blocking means and said contact means; and
    said contact means includes a transmission wire coupled to said rearwardly disposed portion and extending to said circuit means in tension through said blocking means passageway for conveying said signal currents and said electrical bias.

9. The instrument of claim 1 including a disposable sterile, thin polymeric cover positionable over said housing for isolating said housing from contaminants.

10. A radiation detection instrument comprising:
    detector means for deriving induced charges in response to gamma ray interaction therewith when selectively biased from a source:
    an integrator network having an input for receiving said induced charges including:
    field effect transistor means having a gate coupled with said input and drain and source terminals for effecting amplification of said induced charges as a signal output at a said terminal;

bipolar transistor means having a base electrode coupled with said field effect transistor, having an emitter terminal coupled with a first impedance selected deriving an operating bias, and a collector terminal responsive to a collector impedance including collector resistor means for effecting amplification of said signal output to derive a voltage amplification signal;

bootstrap transistor stage means responsive to couple energy corresponding with said signal output to said collector resistor mens for raising the effective said collector impedance in correspondence therewith; and capacitor means coupled intermediate said integrator output and input for providing a capacitance of value selected as below about one picofarad.

11. The instrument of claim 10 in which said capacitor means has a capacitance of about 0.25 picofarad.

12. The instrument of claim 10 in which said detector means includes:

a gamma radiation responsive crystal;

a source of select bias voltage;

a circuit supply source of first polarity and ground;

first resistor means exhibiting a resistance within a range of about 10 to 200 megohms coupled intermediate said bias source and said crystal;

coupling capacitor means coupled intermediate said gate terminal and said crystal;

second resistor means exhibiting a resistance within the range of about 10 to 10,000 megohms coupled intermediate said gate terminal and said supply source ground for effecting bias at said field effect transistor input amplification means.

13. The instrument of claim 12 in which: said first and second resistor means are mounted upon the surface of a circuit support; and said coupling capacitor means is located in space above said surface.

14. The instrument of claim 13 in which said first and second resistor means extend in space from said support surface and support said coupling capacitor means for said location in space above said support surface.

15. The instrument of claim 10 including:

a circuit supply source consisting of first polarity and ground; and wherein said first impedance includes a bias resistor and a capacitor coupled in parallel circuit relationship therewith coupled between said emitter terminal and ground.

16. The instrument of claim 10 in which:

said collector impedance includes bootstrap capacitor means coupled with said collector resistor means for coupling said energy thereto; and said bootstrap transistor stage means includes a base coupled for response to potential derived at said collector resistor means and an output terminal coupled with said bootstrap capacitor means for transferring said energy thereto.

17. Apparatus for detecting sources of gamma radiation comprising:

a housing having a forward portion extending to a forward opening positionable proximate said source, and a rear portion extending from said forward portion;

window means for permitting transmission of said radiation through said forward opening;

a crystal responsive to said radiation, positioned within said forward portion, having a forward surface disposed toward said window means and a rearward surface;

electrically conductive contact means positioned adjacent said crystal rearward surface for effecting application of electrical bias thereto and conducting gamma ray induced charge signals therefrom;

circuit means within said housing rear portion including:

a source of select bias voltage and ground;

connection means coupled with said contact means for applying said bias thereto and conveying said charge signals;

an integrator network having an input coupled with said connection means and including:

field effect transistor means having a gate coupled with said input and drain and source terminals for effecting amplification of said induced charges as signal output at a said terminal;

bipolar transistor means having a base electrode coupled with said field effect transistor, having an emitter terminal coupled with a first impedance selected deriving an operating bias, and a collector terminal responsive to a collector impedance including collector resistor means for effecting amplification of said signal output to derive a voltage amplification signal;

bootstrap transistor stage means responsive to couple energy corresponding with said signal output to said collector resistor means for raising the effective said collector impedance in correspondence therewith;

capacitor means coupled intermediate said integrator output and input for providing a capacitance of value selected as below about one picofarad; and transmission circuit means for treating and transmitting said amplified voltage signals.

18. The apparatus of claim 17 including:

a circuit supply source consisting of first polarity and ground; and wherein said first impedance includes a bias resistor and a capacitor coupled in parallel circuit relationship therewith coupled between said emitter terminal and ground.

19. The apparatus of claim 18 in which:

said collector impedance includes bootstrap capacitor means for coupling said energy thereto; and said bootstrap transistor stage means includes a base coupled for response to potential derived at said collector resistor means and an output terminal coupled with said bootstrap capacitor means for transferring said energy thereto.

20. The apparatus of claim 18 in which:

said first and second resistor means are mounted upon the surface of a circuit support; and said coupling capacitor means is located in space above said surface.

21. The apparatus of claim 20 in which:

said first and second resistor means extend in space from said support surface and support said coupling capacitor means for said location in space above said support surface.

22. The apparatus of claim 21 in which said circuit means includes:

first resistor means exhibiting a resistance selected in a range of about 10 to 200 megohms coupled intermediate said bias source and said connection means; and coupling capacitor means coupled intermediate said gate and said connection means.

23. The apparatus of claim 22 in which said integrator network includes second resistor means exhibiting a resistance selected within a range of about 10 to 10,000 megohms coupled with said gate terminal for effecting a bias at said field effect transistor.

24. Apparatus for detecting and evaluating sources of gamma radiation having given energy levels, comprising:

detector means for deriving induced charges in response to interactions of said radiation therewith to provide detector signals of given levels and exhibiting noise characteristics of given levels;

noise averaging means responsive to said given noise characteristics for deriving a noise signal corresponding with an average level of said given noise characteristic levels;

normalizing circuit means responsive to said detector signals and given noise characteristics and to a control input for adjusting the level of said noise characteristics and corresponding said detector signal given levels to provide composite signals of normalized values;

comparator means responsive to said composite signals for comparing the amplitude thereof with presettable upper and lower threshold levels for providing pulse data outputs corresponding with said comparisons;

logic circuit means responsive to said pulse data outputs for deriving valid pulse signals;

output means controllable for providing a valid pulse signal related perceptible output; and control means responsive to said noise averaging means noise signal for deriving said control input to said normalizing circuit means and to said valid pulse signals for controlling said output means.

25. The apparatus of claim 24 in which said control means is responsive to said noise averaging means noise signal to preset said lower threshold level at a value at least as high as said noise signal.

26. The apparatus of claim 24 including:

pulse acquire means responsive to said composite signals to provide peak signal values corresponding with the instantaneous highest given level of said detector signals; and said control means is responsive to said peak signal values to preset said upper threshold level in correspondence therewith.

27. The apparatus of claim 24 including:

pulse generating network means actuable for generating a diagnostic pulse of controlled amplitude and width; and said control means is configured for selectively actuating said pulse generating network means and diagnostically monitoring said noise averaging means, said normalizing circuit means and said comparator means.

28. A system for detecting and locating sources of gamma radiation, comprising:

a hand manipular probe including:

a housing having a forward portion extending to a window positionable in the vicinity of said source and a hand graspable portion extending from said forward portion;

detector circuit means within said housing for deriving induced charges in response to gamma ray interaction therewith and providing output signals corresponding therewith, and transmission means for transmitting said output signals; and signal treatment means including:

energy level analysis network means for evaluating said output signals with respect to noise phenomena and deriving pulse data output signals;

annunciator means responsive to drive signals for providing an audibly perceptible output variable in response to the frequency of said drive signals; and control means responsive to said pulse data output signals for deriving the rates of occurrence thereof for predetermined intervals and responsive to each discrete said derived rate for generating a predetermined corresponding said drive signal of unique frequency.

29. The system of claim 28 in which said control means drive signal unique frequency is selected to increase in frequency value in correspondence with increasing said derived rates of occurrence of said pulse data output signals.

30. An instrument for detecting and locating sources of radiation emission, comprising:

a housing having a first portion having sidewalls formed of select gamma radiation attenuating material and exhibiting an electrical shielding effect and extending to a forward opening positionable proximate said source, and a hand graspable second portion extending from said first portion;

window means for permitting gamma radiation transmission through said forward opening while blocking the passage of light;

a gamma radiation responsive crystal positioned within said first portion having a forward surface disposed toward said window means for exposure to said radiation emission and a rearward surface;

a thin, gamma radiation transmissive and electrically conductive first insert provided as a sheet of carbon filled silicon rubber positioned adjacent said crystal forward surface;

electrically conductive contact means positioned adjacent said crystal rearward surface for effecting application of an electrical bias thereto and conducting gamma ray induced signal charges therefrom and having a rearwardly disposed portion;

blocking means formed of a gamma radiation attenuating material positioned within said housing first portion and adjacent said contact means rearwardly disposed portion for blocking entry of radiation toward said crystal rearward surface;

compression means within said housing first portion for effecting a conforming compressive relationship between said crystal forward surface and said first insert and between said crystal rearward surface and said contact means; and circuit means within said housing for applying said electrical bias through said contact means, and including amplifier means and for receiving and electrically treating said signal charges to provide output signals.

31. The instrument of claim 30 in which said compression means comprises a compressible foamaceous material.

32. The instrument of claim 30 in which said compression means comprises a compressible foamaceous material and a retainer transparent to said radiation retaining said foamaceous material in compression against said crystal forward surface.

33. The instrument of claim 32 in which said compression means is spaced from said window means a predetermined amount establishing a dead air space therebetween.

34. The instrument of claim 30 in which said foamaceous material is electrically conductive, is positioned in compression intermediate said window means and said first insert.

35. The instrument of claim 34 in which said circuit means includes an electrical path for applying electrical ground to said housing first portion, said crystal forward surface, said first insert and said foamaceous material.

36. The instrument of claim 30 in which:
said blocking means is formed of a slug of said radiation attenuating material slideably insertable within said housing first portion and having a passageway formed therethrough;
including insulating means intermediate said blocking means and said contact means; and
said contact means includes a transmission wire coupled to said rearwardly disposed portion and extending to said circuit means in tension through said blocking means passageway for conveying said signal currents and said electrical bias.

37. The instrument of claim 30 including a disposable sterile, thin polymeric cover positionable over said housing for isolating said housing from contaminants.

38. An instrument for detecting and locating sources of radiation emission, comprising:
a housing having a first portion having sidewalls formed of select gamma radiation attenuating material and exhibiting an electrical shielding effect and extending to a forward opening positionable proximate said source, and a hand graspable second portion extending from said first portion;
window means for permitting gamma radiation transmission through said forward opening while blocking the passage of light;
a gamma radiation responsive crystal positioned within said first portion having a forward surface disposed toward said window means and a rearward surface;
a thin, gamma radiation transmissive and electrically conductive first insert positioned adjacent said crystal forward surface;
electrically conductive contact means positioned adjacent said crystal rearward surface for effecting application of an electrical bias thereto and conducting gamma ray induced signal charges therefrom and having a rearwardly disposed portion;
a thin compliant, adherent electrically conductive second insert intermediate said contact means and said crystal rearward surface;
blocking means formed of a gamma radiation attenuating material positioned within said housing first portion and adjacent said contact means rearwardly disposed portion for blocking entry of radiation toward said crystal rearward surface;
compression means within said housing first portion for effecting a conforming compressive relationship between said crystal forward surface and said first insert and between said crystal rearward surface and said contact means; and
circuit means within said housing for applying said electrical bias through said contact means, and including amplifier means and for receiving and electrically treating said signal charges to provide output signals.

39. A radiation detection instrument comprising:
detector means for deriving induced charges in response to gamma ray interaction therewith when selectively biased from a source:
an integrator network having an input for receiving said induced charges including:
field effect transistor means having a gate coupled with said input and drain and source terminals for effecting amplification of said induced charges as an output at a said terminal;
bipolar transistor means having a base electrode coupled with a said field effect transistor terminal and having first and second select impedances coupled with the respective collector and emitter terminals thereof for deriving a first votlage amplification signal as a voltage amplification of said field effect transistor output; and
capacitor means coupled intermediate said integrator output and input for providing a capacitance of value selected as below about one picofarad, and being provided having a coaxial structure including a conductive tube forming one side thereof and a conductive wire insertable a select distance within and spaced from said tube forming the opposite side thereof.

* * * * *